United States Patent
Maidment et al.

(10) Patent No.: US 9,743,891 B2
(45) Date of Patent: Aug. 29, 2017

(54) SUPER-RESOLUTION TOMOSYNTHESIS IMAGING SYSTEMS AND METHODS

(71) Applicants: THE TRUSTEES OF THE UNIVERSITY OF PENNSYLVANIA, Philadelphia, PA (US); REAL TIME TOMOGRAPHY, LLC, Villanova, PA (US)

(72) Inventors: Andrew D. A. Maidment, Villanova, PA (US); Raymond J. Acciavatti, Newtown Square, PA (US); Predrag Bakic, Philadelphia, PA (US); Susan Ng, Villanova, PA (US); Peter A. Ringer, Allentown, PA (US); Johnny Kuo, Lancaster, PA (US)

(73) Assignees: The Trustees of the University of Pennsylvania, Philadelphia, PA (US); Real Time Tomography, LLC, Villanova, PA (US)

( * ) Notice: Subject to any disclaimer, the term of this patent is extended or adjusted under 35 U.S.C. 154(b) by 0 days.

(21) Appl. No.: 14/413,279

(22) PCT Filed: Jul. 9, 2013

(86) PCT No.: PCT/US2013/049789
§ 371 (c)(1),
(2) Date: Jan. 7, 2015

(87) PCT Pub. No.: WO2014/011681
PCT Pub. Date: Jan. 16, 2014

(65) Prior Publication Data
US 2015/0201890 A1    Jul. 23, 2015

Related U.S. Application Data

(60) Provisional application No. 61/669,459, filed on Jul. 9, 2012, provisional application No. 61/763,310, filed on Feb. 11, 2013.

(51) Int. Cl.
*A61B 6/02* (2006.01)
*A61B 6/00* (2006.01)

(52) U.S. Cl.
CPC ............ *A61B 6/025* (2013.01); *A61B 6/4233* (2013.01); *A61B 6/4452* (2013.01); *A61B 6/502* (2013.01); *A61B 6/54* (2013.01)

(58) Field of Classification Search
CPC ........................................................ A61B 6/03
See application file for complete search history.

(56) References Cited

U.S. PATENT DOCUMENTS 7,817,773 B2    10/2010    Stanton et al.
8,233,690 B2    7/2012     Ng et al.
(Continued)

FOREIGN PATENT DOCUMENTS

JP    10-314161         12/1998
WO   WO 2012/077694    6/2012

OTHER PUBLICATIONS

International Search Report and Written Opinion for PCT/US2013/049789 mailed Dec. 30, 2013.
(Continued)

*Primary Examiner* — Matthew Bella
*Assistant Examiner* — Brian Shin
(74) *Attorney, Agent, or Firm* — RatnerPrestia

(57) ABSTRACT

Tomosynthesis imaging methods, systems, and apparatus include a source to emit penetrating particles toward an object, a detector to acquire a series of projection images responsive to the penetrating particles, and a positioning system to position the source with respect to the object and the detector. An imaging system controls the positioning apparatus, source, and detector to acquire images along a primary scan direction with offsets in a secondary scan direction. An oscillatory velocity may be applied to the
(Continued)

source to reduce focal spot blur. Tomographic volumes are constructed that are capable of exhibiting super-resolution from data representing the acquired series of projection images taking the primary scan direction and the offsets into consideration.

14 Claims, 16 Drawing Sheets

(56) References Cited

U.S. PATENT DOCUMENTS

| | | | |
|---|---|---|---|
| 2005/0175143 A1* | 8/2005 | Miyazaki | A61B 6/032 378/19 |
| 2005/0226369 A1 | 10/2005 | Martin et al. | |
| 2010/0067822 A1* | 3/2010 | Young | G06T 3/4069 382/264 |
| 2011/0026667 A1 | 2/2011 | Poorter | |
| 2011/0069812 A1* | 3/2011 | Takahashi | A61B 6/025 378/21 |
| 2012/0014498 A1 | 1/2012 | Akahori | |

OTHER PUBLICATIONS

Rafferty, E.: "Tomosynthesis: New Weapon in Breast Cancer Fight." Imaging Economics 17(4), 2004.

Acciavatti, R.J., Maidment, A.D.A.: "Investigaing the Potential for Super-resolution in Digital Breast Tomosynthesis," In: Pelc, N.J., Samei, E., Nishikawa, R,M. (eds) Proc. of SPIE, Medical Imaging 2011: Physics of Medical Imaging, vol. 7961, pp. 79615K-1-79615K-12, SPIE, Belllingham (2011).

Lee, D.L., Cheung, L.K., Rodricks, B., Powell, G.F.: "Improved imaging performance of a 14×17-inch Direct Radiography™ System using Se/TFT detector." In: Dobbins III, J.T., Boone, J.M. (eds.) Proc. of SPIE, Medical Imaging 1998: Physics of Medical Imaing, vol. 3336, pp. 14-23. SPIE, Bellingham (1998).

Stewart, J.: "Calculus: Early Transcendentals." Belmont (2003). Book.

Zhao, B., Zhao, W.: "Three-dimensional linear system analysis for breast tomosynthesis." Med. Phys. 35(12), 5219-5232 (2008).

Barrett, H.H., Myers, K.J.: "Foundations of Image Science." Bahaa E.A. Saleh, Hoboken (2004). Book.

\* cited by examiner

SUPER-RESOLUTION TOMOSYNTHESIS IMAGING SYSTEMS AND METHODS

CROSS REFERENCE TO RELATED APPLICATIONS

This application claims priority to U.S. Provisional application Ser. No. 61/669,459 entitled TOMOSYNTHESIS ACQUISITION SYSTEM OPTIMIZED FOR SUPER-RESOLUTION, filed on Jul. 9, 2012, and to U.S. Provisional application Ser. No. 61/763,310 entitled TOMOSYNTHESIS ACQUISITION SYSTEM OPTIMIZED FOR SUPER-RESOLUTION, filed on Feb. 11, 2013, which are both incorporated fully herein by reference.

STATEMENT REGARDING FEDERALLY SPONSORED RESEARCH

This invention was made in whole or in part with government support under Grant Number W81XWH-11-1-0100, through the Department of Defense Breast Cancer Research Program. The government may have rights in this invention.

BACKGROUND INFORMATION

In digital tomosynthesis (DT), a 3-dimensional image of an object or anatomy is typically generated from a limited number of low-dose x-ray projections acquired from different angles. The x-ray source is typically moved in an arc around an object being imaged (such as a breast) while a series of projection images are captured with a detector including an array of pixels. The arc is along a scan direction that is aligned with rows of pixels within the pixel array. Data from the resultant projection images is then processed by a computer to create a 3-dimensional tomographic volume. In breast imaging, digital breast tomosynthesis (DBT) has been shown to improve sensitivity and specificity for cancer detection relative to traditional two-dimensional projection mammography. In chest imaging, DT has been shown to improve the sensitivity and specificity of lung nodule detection relative to traditional two-dimensional projection radiography. DT has also had value in musculoskeletal imaging and in non-destructive testing.

DT's oblique x-ray incidence shifts the image of features within an object in sub-pixel detector element increments along the scan direction with each projection angle. As a result of this property, DT is capable of "super-resolution", a term which is used to denote sub-pixel resolution, i.e., resolution that is finer than the physical size of the detector elements. Although super-resolution is achievable over a broad range of positions along the scan direction (e.g., parallel to the chest wall side of the breast support in current DBT systems), it cannot be achieved over a broad range of positions perpendicular to the scan direction (e.g., the chest wall—nipple direction in current DBT systems). This is because, for example, in current DBT systems the translational shifts in the image between projections are minimal or non-existent in the posteroanterior (PA) direction.

Higher resolution images are useful in the accurate detection and diagnosis of cancer, bone fractures, and other fine details. In breast imaging, for example, the presence of lesions, such as microcalcifications, can indicate the early stage of breast cancer. The form and morphology of the microcalcifications are important factors in determining whether the microcalcifications are benign or malignant. Improved visibility and conspicuity of lesions help in the determination of the probability of malignancy. It is therefore desirable to determine and set acquisition parameters to optimize super-resolution.

In DT x-ray systems, there are two acquisition modes for x-ray tube motion: step and shoot motion (SSM) and continuous tube motion (CTM). For a rapid scan time, SSM systems are mechanically limited. CTM systems reduce the scan time but the movement of the x-ray tube during exposures produces focal spot blur which can result in image blurring. The effect of blurring can limit the spatial resolution and reduce the visibility of details.

SUMMARY OF THE INVENTION

Super-resolution tomosynthesis imaging methods, systems, and apparatus are disclosed. A super-resolution digital tomosynthesis system for imaging an object may include at least one source configured to emit penetrating particles toward an object, at least one detector comprising an array of pixels configured to acquire a series of projection images of the object in response to the penetrating particles from the at least one source, positioning apparatus configured to position the at least one source relative to the object and the detector, and an imaging system coupled to the at least one source, the at least one detector, and the positioning apparatus. The imaging system may control the positioning apparatus to position the at least one source relative to the object and the at least one detector along a primary scan direction and to introduce at least one offset along a secondary scan direction with at least one offset being a non-integer multiple of a pixel dimension within the array of pixels, to control the at least one source and the at least one detector to acquire the series of projection images along the primary scan direction with the introduced at least one offset, and to construct a tomographic volume capable of exhibiting super-resolution from data representing the acquired series of projection images taking the primary scan direction and the at least one offset into consideration. An oscillatory velocity may be applied to the at least one source to reduce focal spot blur.

A super-resolution digital tomosysnthesis method for imaging an object may include positioning at least one source of penetrating particles relative to at least one detector and the object along a primary scan direction, the at least one detector comprising an array of pixels, introducing at least one offset in a secondary scan direction as the at least one source of penetrating particles relative to the object and the at least one detector is positioned along the primary scan direction, at least one offset being a non-integer multiple of a pixel dimension within the array of pixels, acquiring a series of images along the primary scan direction with the introduced at least one offset, and constructing a tomographic volume capable of exhibiting super-resolution from data representing the acquired series of projection images taking the primary scan direction and the at least one offset into consideration.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. The letter "n" may represent a non-specific number for elements. Also, lines without arrows connecting components may represent a bi-directional exchange between these components. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Figure 1:
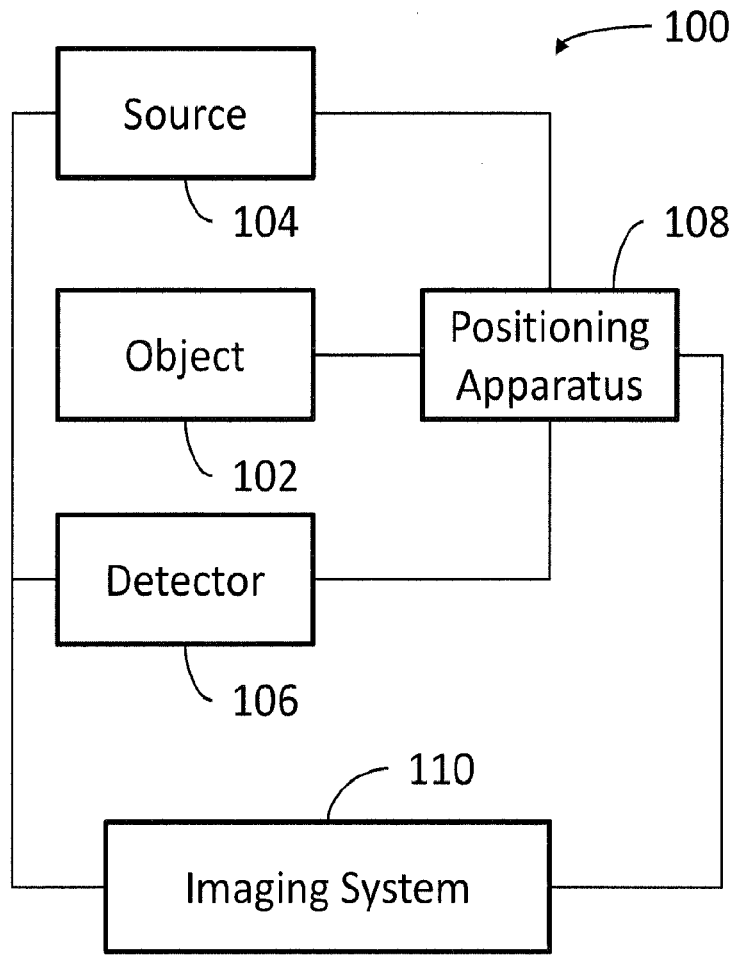
FIG. 1 is a block diagram of a tomosynthesis system for imaging an object in accordance with aspects of the invention.

FIG. 1 depicts a tomosynthesis system 100 for imaging an object 102 in accordance with aspects of the invention. In an embodiment, the object 102 is a human breast. In other embodiments, the object may be other anatomical features of a living being or may be an inanimate object (e.g., luggage).

The illustrated system 100 includes a source 104 that emits penetrating particles toward a detector 106, with the object positioned in between the source 104 and the detector 106. Penetrating particles that pass through the object 102 create a projection image of the object on the detector 106. The penetrating particles may be x-rays, photons, neutrons, beta particles, or other particles capable of passing through the object and creating a projection image on a detector 106.

The source 104 may be a conventional x-ray tube configured to emit x-rays toward the object 102 and the detector 106. The detector 106 may be a conventional x-ray detector including an array of pixels. The array of pixels may be square, another geometric shape, a combination of geometric shapes, or irregular. Additionally, the array of pixels may be formed from a two-dimensional array of pixels or a series of one-dimensional arrays of pixels. Other suitable sources 104 and detectors 106 (e.g., those capable of emitting and detecting other penetrating particles) will be understood by one of skill in the art from the description herein. Additionally, although a single source 104 and a single detector 106 are illustrated, additional sources 104 and detectors 106 may also be employed.

Positioning apparatus 108 is coupled to the object 102 (e.g., via a support member for the object 102, which is described in further detail below), the source 104, and/or the detector 106. As described in further detail below, the positioning apparatus 108 is configured to position the source 104 relative to the object 102 and the detector 106 along a primary scan direction and to introduce an offset along a secondary scan direction. In use, the source 104 emits penetrating particles at a series of locations along the primary scan direction. The offset is introduced as the source travels along the primary scan direction such that the image projections in the series of locations are offset on the pixel array by a non-integer multiple of a pixel dimension such as width. For example, if a pixel has a length, l, the offset between adjacent images in the series may be 0.1 l, 0.2 l, 1/16 l, etc. The sub-pixel offsets enable construction of a tomographic volume capable of exhibiting super-resolution.

In an embodiment, the object 102 remains stationary and the positioning apparatus is coupled to the source 104 to move the source 104 along a primary scan direction and is coupled to the detector 106 to move the detector 106 along a secondary scan direction (see, for example, FIGS. 2, 4A, 4B, and 4C and the related description). In another embodiment, the positioning apparatus is coupled to the source 104 to move the source 104 along the primary scan direction and in the secondary scan direction (see, for example, FIGS. 5A and 5B and the related description). In another embodiment, the positioning apparatus is coupled to the object 102 (e.g., a conveyer belt with the object 102 positioned thereon) to move the object 102 along the primary scan direction; and a series of detectors, each detector including pixels, that are physically offset by a non-integer multiple of the pixel width to create an offset in the secondary scan direction (see FIGS. 6A and 6B and the related description). Other suitable arrangements to position the source 104 relative to the object 102 and the detector 106 will be understood by one of skill in the art from the description herein and are considered within the scope of the invention.

An imaging system 110 is coupled to the source 104, the detector 106, and the positioning apparatus 108. The imaging system 110 instructs the positioning apparatus 108 to position the object 102/source 104/detector 106 along the primary scan direction with an introduced offset in the secondary scan direction, instructs the source 104 to emit penetrating particles, captures data from the detector 106 representing projection images of the object 102 responsive to the emitted penetrating particles, and constructs a tomographic volume of the object that is capable of exhibiting super-resolution. Additionally, the imaging system may display super-resolution images generated from the tomographic volume. The imaging system 110 may include, for example, user input devices such as a keyboard and a mouse for receiving operator instructions to manipulate images, user output devises such as a display for displaying super-resolution images, and an internal and/or external memory for storing instructions for implementing one or more of the steps described herein, for storing data from acquired images, and for storing constructed tomographic volumes. Suitable input and output devices and memory will be understood by one of skill in the art from the description herein.

Figure 1A:
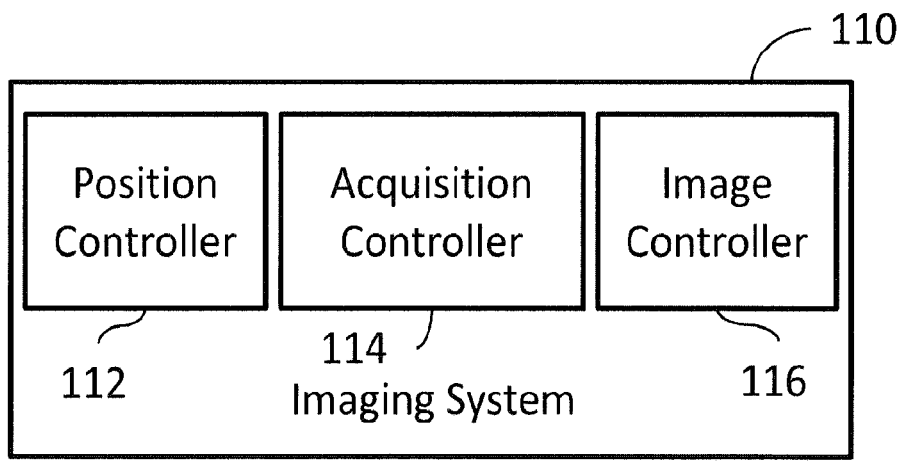
FIG. 1A is a block diagram of an imaging system for use in the tomosynthesis system of FIG. 1 in accordance with aspects of the invention.

FIG. 1A depicts the imaging system 110 in further detail. The illustrated imaging system 110 in FIG. 1A includes a position controller 112, an acquisition controller 114, and an image controller 116. The position controller 112 may control positioning apparatus 108 to position the object 102, the source 104, and/or the detector 106 relative to one another to enable a series of images to be captured along a primary scan direction with an introduced offset in a secondary scan direction.

The acquisition controller 114 may control the source 104 and the detector 106 to respectively emit penetrating particles and capture projected images of the object 102 responsive to the emitted penetrating particles. The acquisition controller may interface with the position controller 112 to ensure the object 102, source 104, and detector 106 are accurately positioned relative to one another during the capture of each of the series of images.

The image controller 116 may process data representing the projected images on the detector 106 to construct a tomographic volume capable of exhibiting super-resolution taking the primary scan direction and the offsets in the secondary scan direction into consideration. Additionally, the image controller 116 may display super-resolution images developed from the tomographic volume.

Although depicted as three separate controllers (position controller 112/acquisition controller 114, and image controller 116) in FIG. 1A, the functionality of these controllers can be performed by more or fewer controllers by one or more processors. Additionally, the controllers/processors may reside in a single housing or may be dispersed across a network.

Figure 2:
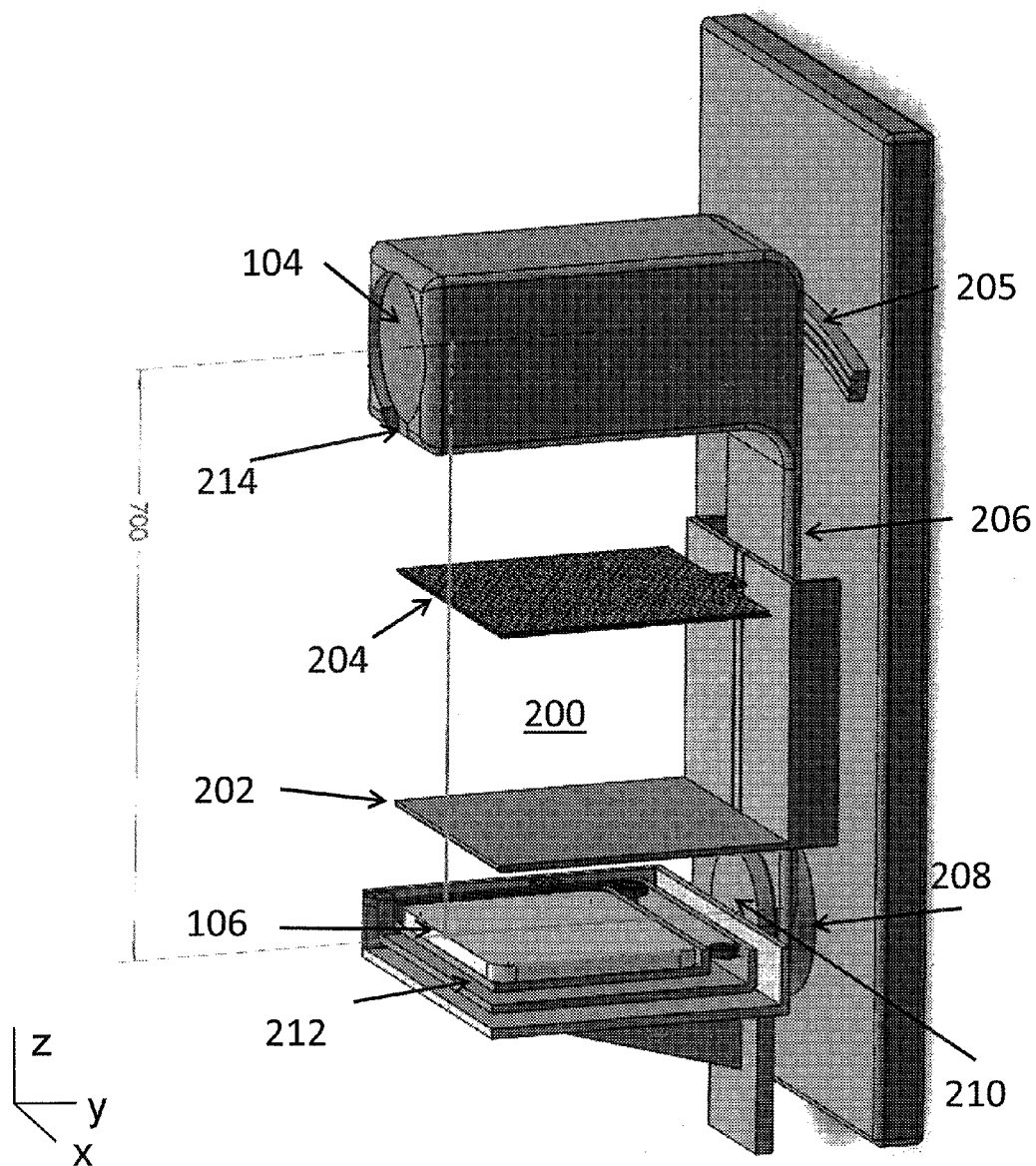
FIG. 2 is a perspective view of a source, detector, and positioning apparatus for use in a tomosynthesis system for imaging an object in accordance with aspects of the invention.

FIG. 2 depicts an embodiment of a source 104, detector 106, and positioning apparatus 108 (FIG. 1) for use in imaging a human breast. Suitable modifications, if any, will be understood for imaging other objects.

A breast may be positioned within an object receiving area 200. The illustrated object receiving area 200 includes a breast support 202, and a compression paddle 204. The breast may be positioned on the breast support 202, which is fixed in position, and the compression paddle 204 may be lowered in a conventional manner into contact with the breast to reduce movement of the breast during the acquisition of images. In an embodiment, the breast support 202 and a movable breast compression paddle 204 are mounted orthogonal to a central ray of penetrating particles emitted by the source 104.

The source 104 illustrated in FIG. 2 includes a conventional x-ray tube and the illustrated detector 106 includes a conventional 2-dimensional x-ray detector.

The positioning apparatus 108 (FIG. 1) in the embodiment illustrated in FIG. 2 includes a primary angular drive 205 coupled to the source 104 to move the source 104 along a primary scan direction (e.g., an arc in the x/z plane) and a micro-positioner 212 coupled to the detector 106 (e.g., via a translational plate) to position the detector 106 to introduce offsets in a secondary scan direction (e.g., in the y direction). The primary angular drive 205 may utilize a servo motor to accurately position the source along the primary scan direction. The illustrated micro-positioner 212 may additionally introduce offset in the x direction (e.g., in the x/y plane). In embodiments where an offset only in a single direction (e.g., in the y direction) is desired, micro-positioner 212 may be a single direction micro-positioner. The addition of micro-positioner 212 allows sub-pixel positioning accuracy for the array of pixels in detector 106. Super-resolution can be optimized by considering the acquisition geometry and the system components.

A micro-positioner 214 is coupled to the source 104 in FIG. 2 that is capable of introducing an offset in the secondary scan direction in addition to or instead of the offsets being introduced by the micro-positioner 212. The micro-positioner may be used to achieve isotropic super-resolution and to compensate for x-ray focus position, e.g., due to position changes associated with x-ray anode temperature fluctuations. For example, during use, x-ray anodes generate heat, which causes them to expand. This expansion causes a shift in the position of the x-ray focus as images are acquired. This shift is known to cause reconstruction artifacts in computed tomography if they are not compensated. Similarly, this shift may cause reconstruction artifacts in DT if they are not compensated. A differential circuit may be employed in embodiments of the invention to compensate for changes in the y position of the focal spot due to expansion of the x-ray anode, for example. This is an improvement over conventional commercial DBT systems, which do not provide compensation due to temperature shifts. One of the significant factors in reconstruction unsharpness of calcifications may be due to temperature shift, e.g., the focal spot will move 0.68 mm for a 500° C. temperature raise in a 100 mm diameter 10° W-target anode x-ray tube.

In embodiments with the micro-positioner 214 coupled to the source 104, the micro-positioner 212 may be omitted. The micro-positioners 212/214 may be amplified piezoelectric actuators.

The micro-positioner 212, with the detector 106 positioned thereon, is coupled to a rotary stage 210 having an axis of rotation that extends along a detection surface of the detector 106. The rotary stage 210 rotates on a slewing bearing 208 that supports the load of the object receiving area 200, the source 104, the detector 106, and the micro-positioners 212/214. A rotary arm 206 is positioned between the source 104 and the detector 106 to maintain the distance there between. Although the axis of rotation is illustrated as extending along the surface of the detector 106, other axes of rotations may be employed, e.g., one extending though the object being imaged. In other embodiments, the primary scan direction may be linear.

Figure 3:
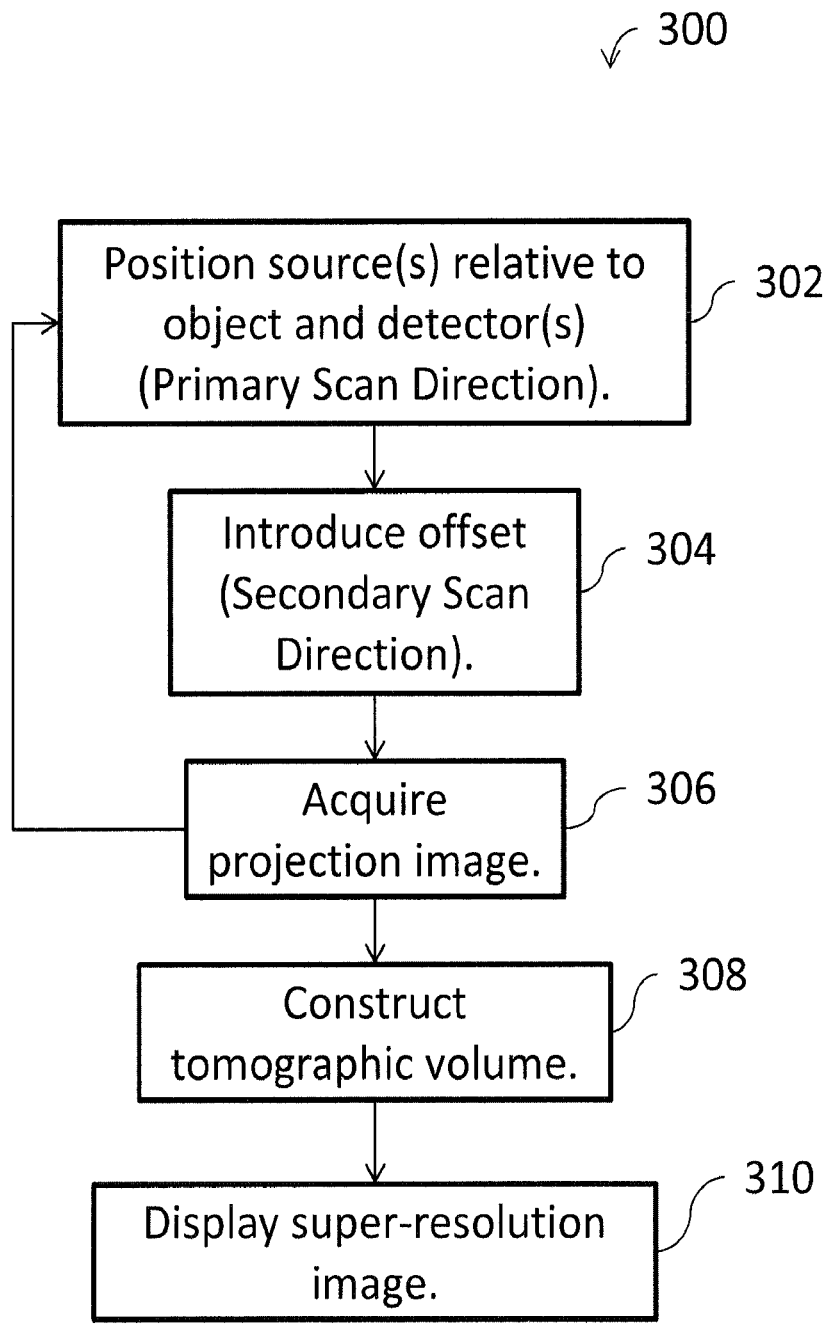
FIG. 3 is a flow chart of tomosynthesis imaging steps for imaging an object in accordance with aspects of the invention.

FIG. 3 depicts a flow chart 300 of exemplary steps for constructing a tomographic volume capable of exhibiting super-resolution taking primary and secondary scan directions into consideration. Although the steps of flow chart 300 are described with reference to the apparatus depicted in FIGS. 1, 1A, and 2, it will be understood that other apparatus may be used in accordance with the invention. Likewise, the apparatus depicted in FIGS. 1, 1A, and 2 may perform other methods. Additionally, in some embodiments, one or more steps of flow chart 300 may be omitted or performed in an order other than depicted (including at the same time).

At block 302, at least one source is positioned relative to the object and at least one detector along a primary scan direction. The at least one source may be a source 104 and the at least one detector may be a detector 106. In one embodiment, the source 104 is configured to move along the primary scan direction with respect to an object 102 and a detector 106. For example, when imaging a breast, the source 104 may be moved along a primary scan direction that is an arc within a plane substantially parallel to the chest wall. In this example, the breast remains stationary during the imaging and the detector 106 may remain stationary or may move such that the detecting surface of the detector 106 is normal to the penetrating rays emitted by the source 104. In another embodiment, the source 104 is stationary and an object 102 and/or a detector 104 may move to create relative movement along the primary scan direction. For example, when imaging luggage, the luggage may be moved past the source 104 along the primary scan direction, e.g., by a conveyer belt.

At block 304, an offset is introduced in a secondary scan direction. The offset may be introduced by positioning the source 104 relative to the detector 106 in the secondary scan direction. In an embodiment, the detector 106 may be moved in the secondary scan direction to position the source 104 relative to the detector 106 in the secondary scan direction. For example, when imaging a breast, the detection surface of the detector 106 may be moved along a secondary direction that is substantially perpendicular (e.g., +/−5%) to the plane of the chest wall. In an embodiment, the source 106 may be moved in the secondary scan direction to position the source 104 relative to the detector 106 in the secondary scan direction. In another embodiment, a series of detectors 106 may be employed with one or more of the detectors 106 offset in order to position the source 104 relative to the detectors 106 along a secondary scan direction.

The offset introduced in step 304 may be introduced at the same time as the positioning is performed in step 302. Alternatively, the steps 302 and 304 may be performed sequentially. The movement of the object 102, the source 104, and/or the detector 106 for positioning along the primary scan direction (step 302) and/or to introduce an offset in the secondary scan direction (step 304) may be a continuous motion, a step-and-shoot motion, or a modulated smooth motion with oscillatory velocity as described in further detail below. The acquisition controller 114 of imaging system 110 may control the movement.

At block 306, a projection image of the object is acquired. Each projection image may be acquired by emitting penetrating particles from the source 104 toward a detector 106 with the object 102 positioned in between. The detector detects the projection image responsive to the emitted penetrating particles that strike the detector surface of the detector 306. The acquisition controller 114 may control acquisition by instructing the source 104 to emit penetrating particles and instructing the detector 106 to capture an image.

If a series of images are being acquired, processing proceeds at step 302, with steps 302-306 repeated until the complete series of projection images is acquired. For example, if nine projection images are to be acquired, steps 302-306 may be performed nine times.

At block 308, a tomographic volume capable of exhibiting super-resolution is constructed from data representing the acquired series of projection images taking the primary scan direction and the introduced offsets into consideration. An imaging system 110, e.g., an image controller 116 may construct the tomographic volume based on data representing the projection images acquired by the detector 106.

Movement of the source 104 relative to the object 102 and the detector 106 results in features within the object being projected onto different positions on the detection surface of the detector 106 in the primary scan direction. See, for example, FIG. 7A and the related description below. The shift in position along the primary scan direction, e.g., lateral to the chest wall during conventional breast imaging, enables super-resolution in the primary scan direction. By introducing an offset in a secondary scan direction, the features within the object are also projected onto different positions of the detection surface of the detector 106 along the secondary scan direction. See, for example, FIG. 7C and the related description below. The shift in position along the secondary scan direction, e.g., in a posteroanterior (PA) direction during breast imaging, enables super-resolution along the secondary scan direction. By combining primary scan direction with the offsets as described herein, tomographic volumes capable of isotropically (i.e., uniformly within the tomographic volume) providing super-resolution images may be constructed.

At block 310, super-resolution images are generated from the constructed tomographic volume. The reconstruction grid should have smaller pixels than the detector in order to achieve super-resolution. The imaging controller 116 of the imaging system 110 may generate super-resolution images under the control of an operator. Additional details regarding generation of super-resolution images are found below and in U.S. Pat. No. 8,233,690 to Ng et al., titled Dynamic Tomographic Image Reconstruction and Rendering On-Demand, which is incorporated fully herein by reference.

Figure 4A:
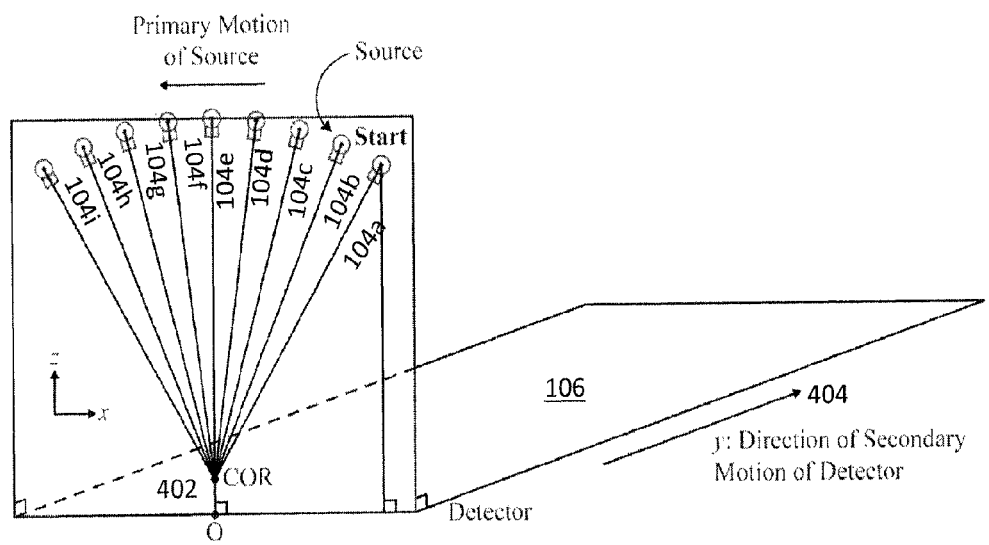
FIGS. 4A and 4B are illustrations depicting movement of a detector from a start position (FIG. 4A) to an end position (FIG. 4B) to introduce an offset in a secondary scan direction in accordance with aspects of the invention.

In the embodiment depicted in FIG. 4A, the source 104 traces a circular arc within the xz plane during a tomosynthesis scan. The source positions are equidistant from a center-of-rotation (COR) 402, which is shown as a point displaced from the surface of the detector 106. The illustrated detector 106 extends along the xy plane, which is orthogonal to the plane of the source motion along a primary scan direction. Although the source motion is semi-circular in this figure, it can be generalized to any trajectory in the xz plane with a primary component of motion along the +x or −x direction. Nine source positions are shown (104a-i); however, the acquisition geometry can be generalized to include any number of source positions.

Figure 4B:
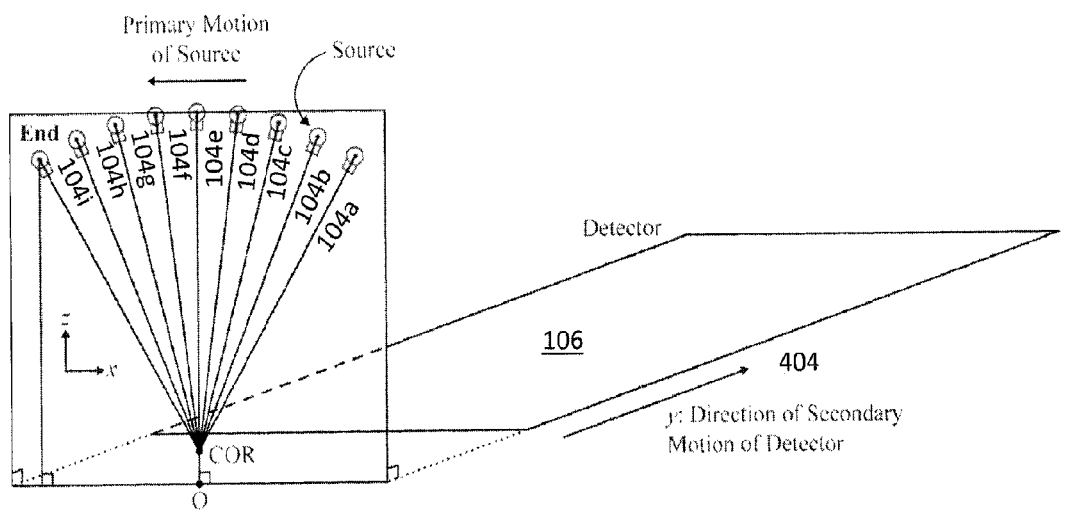

Due to the motion of the source along the primary scan direction relative to the object, when present, and the surface of the detector 106, there are shifts in the features of the object along the x direction, allowing for super-resolution along this direction. To achieve sub-pixel sampling gain along a secondary direction (i.e., the y direction in this illustration), the detector 106 is translated along the y direction (as shown in FIG. 4B). The secondary motion of the detector 106 promotes shifts in the image of an object along the y direction with each projection. The detector 106 should be translated in sub-pixel multiples of detector element (del) length with each projection in order to promote sub-pixel resolution (i.e., super-resolution). The motion of the detector 106 can be designed with either discrete or continuous translations during the tomosynthesis scan.

Figure 4C:
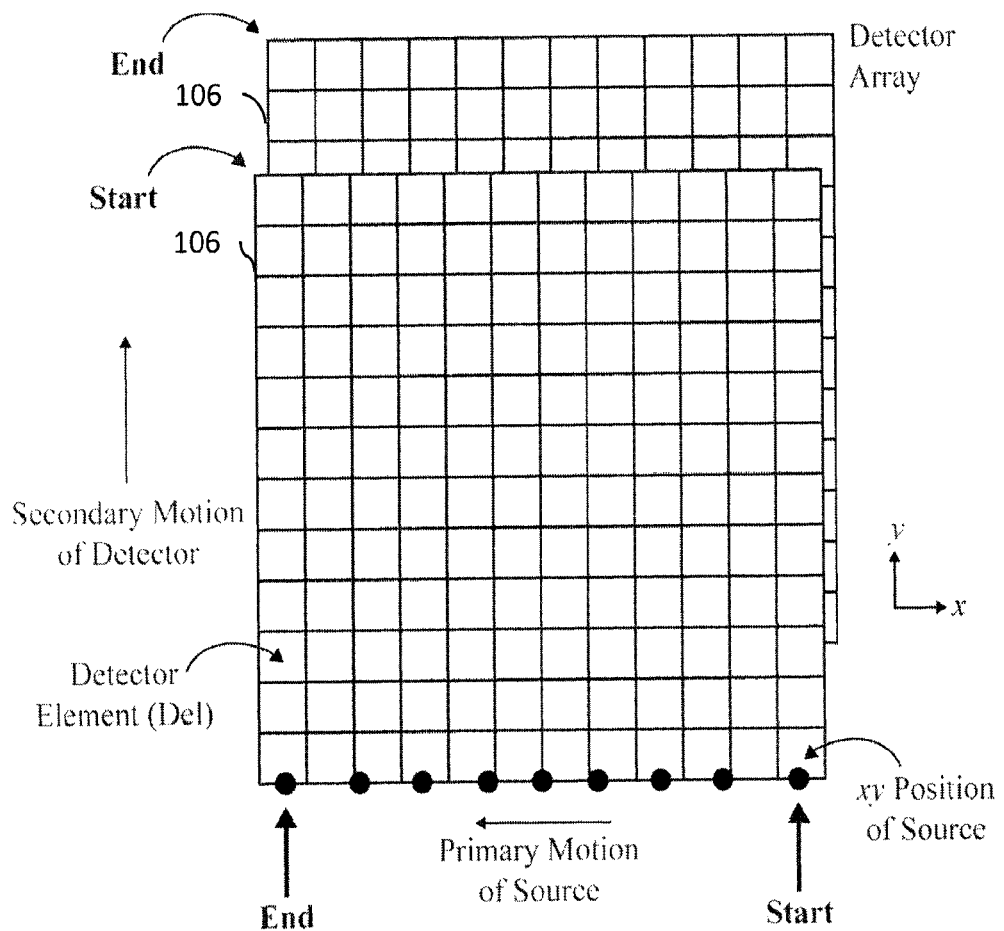
FIG. 4C is an illustration of the relative change in position of the detector from FIGS. 4A and 4B.

A cross section of the planar surface of the detector is depicted in FIG. 4C before the introduction of an offset (FIG. 4A) and after the introduction of an offset (FIG. 4B). FIG. 4C illustrates that the source positions extend along only one direction (primary direction, x). To promote super-resolution along the y direction, secondary motion for the detector is introduced along the y direction. The increment of detector translation between projections is a sub-pixel multiple of detector element (del) length. This setup promotes super-resolution along the y direction due to the translational shifts in the image of the object between projections. In one embodiment, the increment of detector translation is constant between projections. In another embodiment, the increments of the detector translation vary between projections.

Figure 5A:
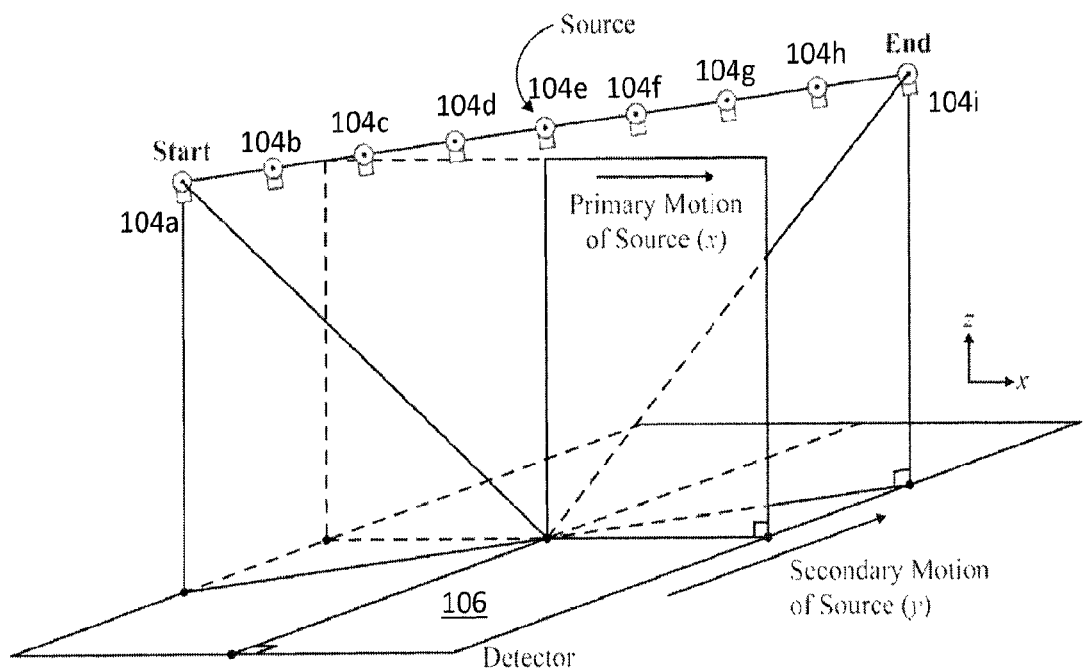
FIG. 5A is an illustration of movement of a source to introduce an offset in a secondary scan direction in accordance with aspects of the invention.

In the acquisition geometry depicted in FIG. 5A, the source 104 is shown with two components of motion: primary motion along the x direction, and secondary motion along the y direction. The detector 106 has extent along the xy plane and can be treated as stationary during tomosynthesis scans. In alternate embodiments, the detector 106 may undergo motion; for example, rotation about the y-axis. The two components of source motion introduce sub-pixel shifts in the imaged features of the object along the x and y directions between projections, promoting super-resolution along both directions. Although the motion of the source is depicted with a straight line, it can be generalized to include an additional component of motion along the z direction. The acquisition geometry can also be generalized for a variable number of source positions (with nine source positions 104a-i shown here for illustration).

Figure 5B:
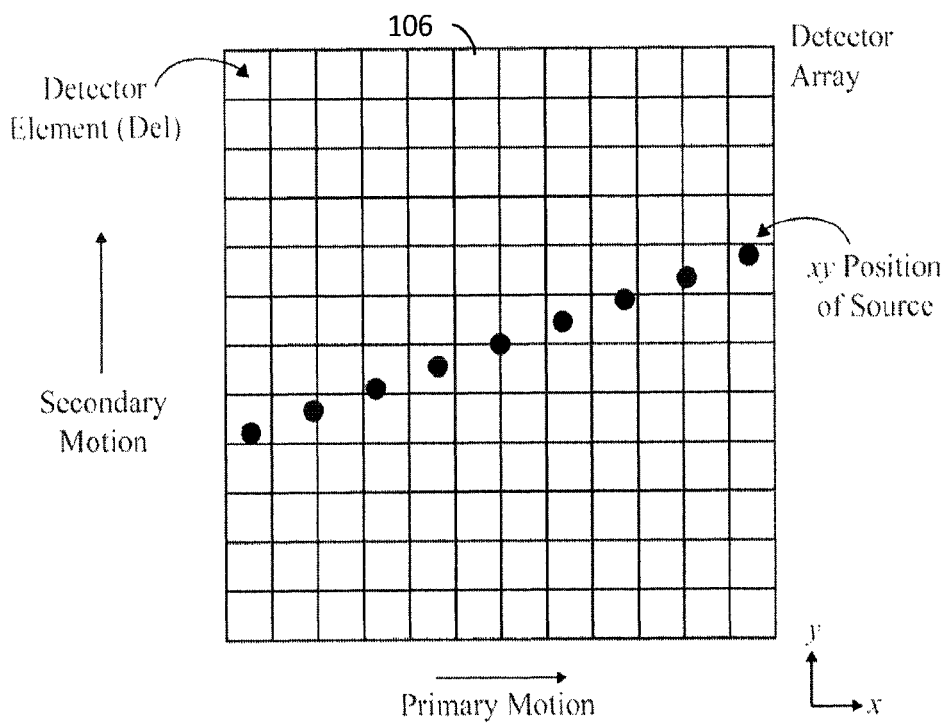
FIG. 5B is an illustration of the relative position of the source and the detector from FIG. 5A.

A cross section of the detection plane of detector 106 is depicted in FIG. 5B for a source 104 having two components of motion as in FIG. 5A. Super-resolution is achievable along both the x and y directions due to shifts in the image of the object between projections occurring in fractional multiples of detector element length (del) along both the x and the y directions.

Figure 6A:
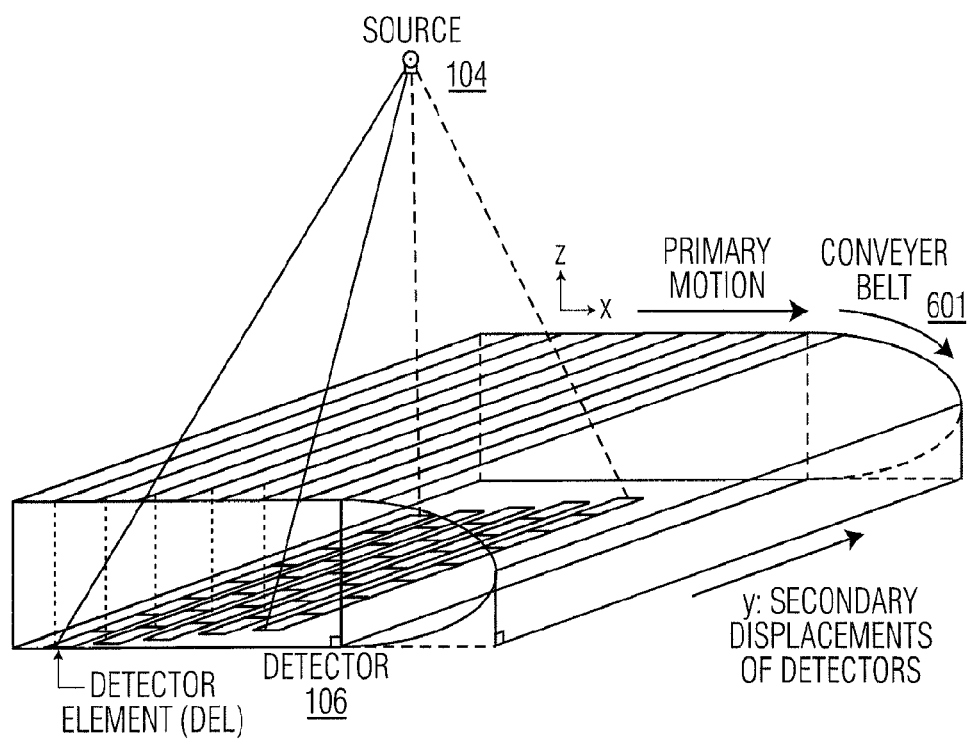
FIG. 6A is an illustration of an object moving relative to a source and a series of offset detectors that introduce an offset in a secondary scan direction in accordance with aspects of the invention.

In the embodiment depicted in FIG. 6A, an object is translated along a conveyer belt during a tomosynthesis scan. The motion of the conveyer belt 601 is along the primary direction (x). Projection images are recorded by linear detectors, which are stationary. The linear detectors are displaced by a fraction of detector element (del) length along the y direction, allowing for sub-pixel sampling gain in the y direction. Super-resolution is achievable along both the x and y directions due to the primary motion of the conveyer belt and the secondary displacements of the detectors, respectively. Although one source is shown in the figure, this setup can be generalized to include multiple sources. This embodiment has value, for example, in luggage scanning. In an alternate embodiment of the source and detectors depicted in FIGS. 6A and 6B, the object can be stationary and the source and detectors can be translated along the object in the primary scan direction. Such an embodiment has value, for example, in non-destructive testing (NDT) of large objects such as aircraft components.

Figure 6B:
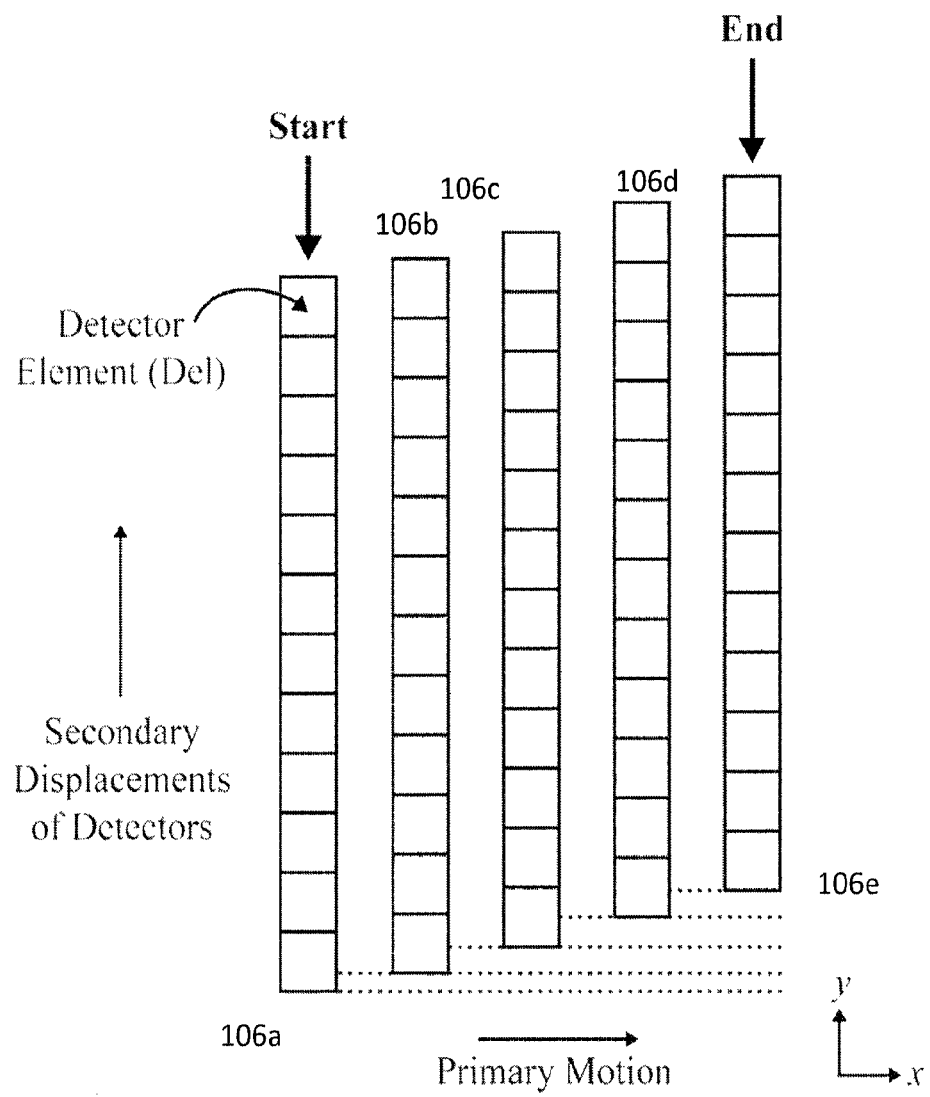
FIG. 6B is an illustration of relative position of the detectors from FIG. 6A.

A cross section of the detector plane depicted in FIG. 6B shows that a series of linear detectors (106a-e) are displaced from each other by a fractional multiple of detector element (del) length along the y direction, which is perpendicular to the primary motion of the conveyer belt. Each linear detector is not necessarily displaced from the others by the same increment. All detector elements are stationary during the tomosynthesis scan. This setup yields super-resolution along both the x and y directions due to the primary motion of the conveyer belt and the secondary displacements of the detectors, respectively.

Figure 7B:
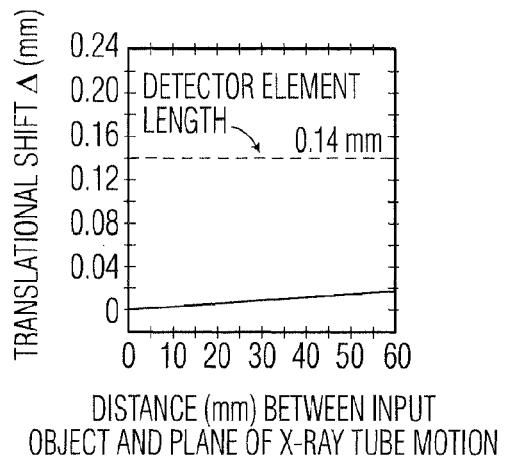
FIG. 7B is a graph depicting the minimal shift away from a primary scan direction with respect to the size of the detector elements within an array of a detector in accordance with the prior art.
Figure 7A:
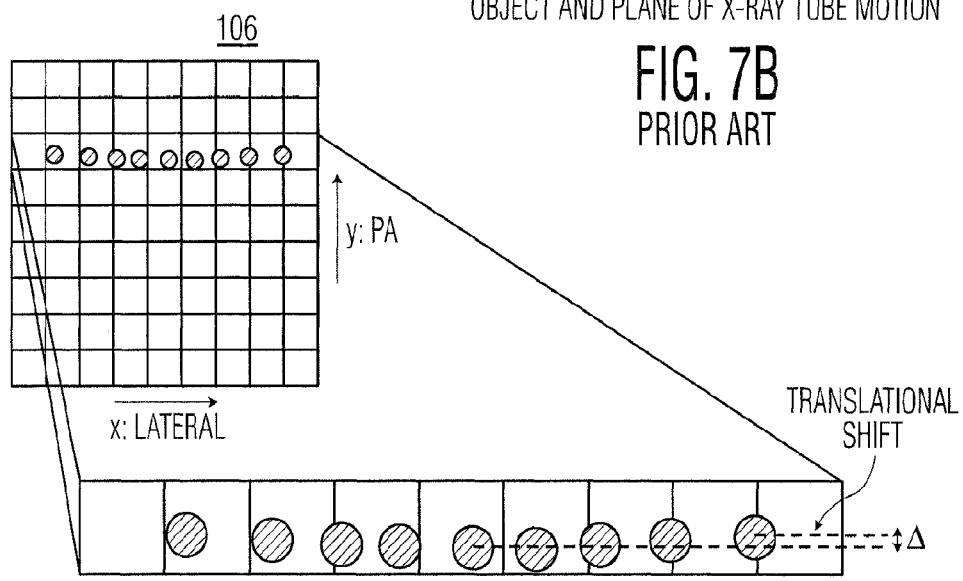
FIG. 7A is an illustration, partly in exploded form, depicting the introduction of lateral sub-pixel shift along a primary scan direction in accordance with the prior art.
Figure 7C:
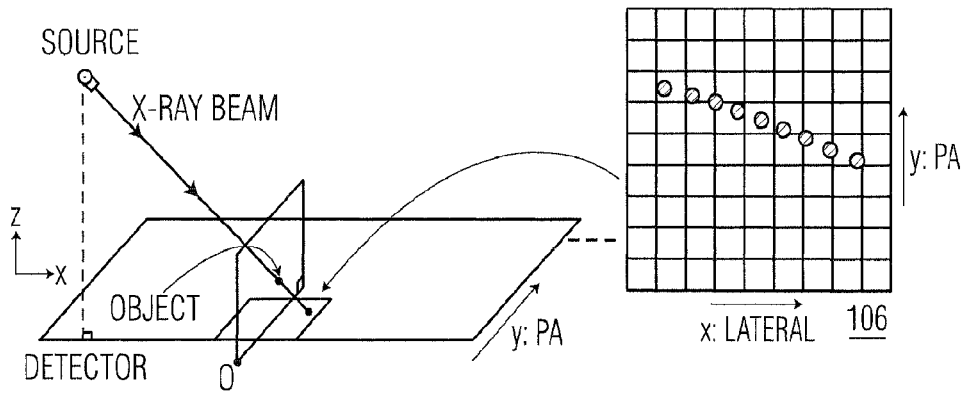
FIG. 7C is an illustration, partly in exploded form, depicting the introduction of lateral sub-pixel shift along a primary scan direction and a secondary motion in a secondary scan direction in accordance with aspects of the invention.

As seen in FIG. 7A, in conventional tomosynthesis systems, the projection of features within an object can introduce sub-pixel shifts in a primary scan direction (e.g., lateral to the chest wall for breast imaging systems) which in total exceed the width of a detector element (del) length in the primary scan direction, enabling super-resolution in the primary scan direction, which is not enabled in other directions such as the posteroanterior (PA) direction for breast imaging systems. Modeling a current clinical DBT system, the translational shift in the image of the object is calculated along the direction perpendicular to the source motion. In comparing the central projection and the most oblique projection as depicted in FIG. 7B, the translational shift in the image does not exceed a single detector element length (0.14 mm). Thus, in conventional DBT systems, super-resolution is not achievable perpendicular to the plane of source motion.

By introducing a small relative motion in a secondary scan direction by moving either the source or detector (see FIG. 7C) in the secondary scan direction such as the PA direction (and hence perpendicular to the conventional primary lateral motion), the conditions needed for isotropic super-resolution can be achieved. Based upon other considerations, such as maximizing the amount of breast tissue imaged, a small number of integer pixel shifts in either the primary or secondary scan direction would not substantially degrade isotropy. Tolerance to imprecisions in the acquisition geometry can be determined by examining the effect of small perturbations in the acquisition on the reconstruction. These considerations and tolerances may be used to determine the manufacturing specifications, and the need for and design of image-based measurements of the acquisition geometry.

Figure 8A:
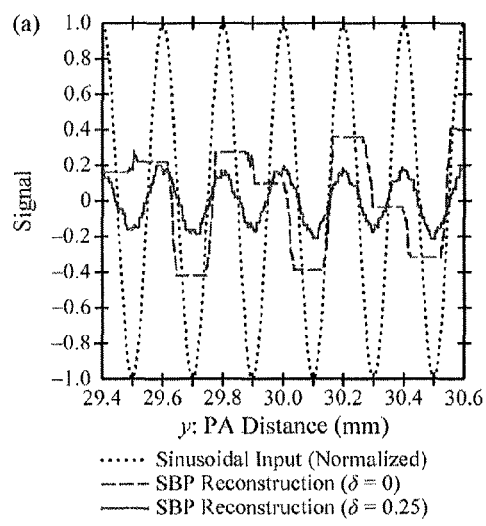
FIGS. 8A, 8B, 8C, and 8D are graphs illustrating that super-resolution is achievable in the posteroanterior (PA) direction by translating the detector between projections in accordance with aspects of the invention.

Additional details for a breast imaging implementation will now be described. One of skill in the art will understand that the concepts described with reference to FIGS. 8A-C, FIG. 9A, and FIG. 9B are applicable to other implementations. As detailed above, in current DBT acquisition geometries, super-resolution does not exist in all directions in the reconstruction. To illustrate analytical treatment of this concept, a sine plate is simulated for an input frequency oriented along the PA direction (FIG. 8A, dotted line). Modeling a current clinical DBT system, a 0.5 mm thick test object at a height of 25.0 mm above the breast support is assumed. An input frequency of 5.0 $mm^{-1}$ was selected since this frequency is higher than the alias frequency of the detector (3.6 mm$^{-1}$ for 140 μm detector elements) and thus demonstrates super-resolution. As shown (FIG. 8A, dashed line), the simple backprojection (SBP) reconstruction resembles a single projection in which signal varies with position in a step-like manner. The width of each step matches the detector element length. As evidence of aliasing, the corresponding Fourier transform (FIG. 8B, dashed line) has a major peak at 2.7 mm$^{-1}$, which is clearly less than the input frequency.

Two embodiments for optimizing super-resolution in DBT are (1) translate the detector in the PA direction during the scan time and (2) modify the trajectory of the source (e.g., x-ray tube) to have extension in the PA direction.

For detector translation, a reconstruction of the 5.0 mm$^{-1}$ input frequency is shown in FIG. 8A. Detector translations of 25% of detector element length (35 μm) between projections are simulated along the PA direction. The reconstruction with this geometry has the overall appearance of a sine wave whose peaks and troughs match the input frequency perfectly (FIG. 8A, solid line). The reconstruction has small variations that can be suppressed by the appropriate choice of a filter. As analytical proof of super-resolution, the major peak of the Fourier transform (FIG. 8C solid line) correctly occurs at the input frequency, 5.0 mm$^{-1}$.

Figure 8B:
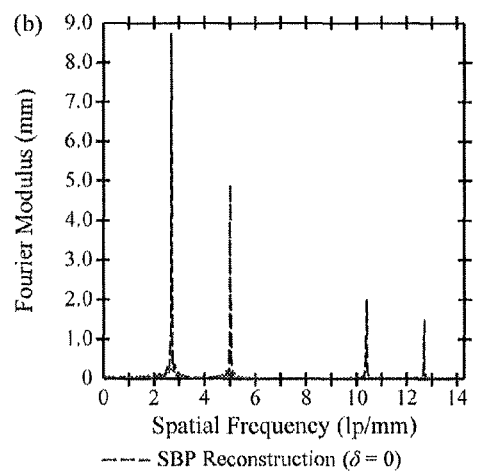
Figure 8C:
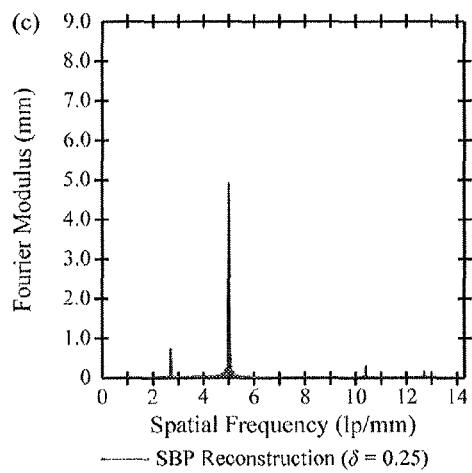
Figure 8D:
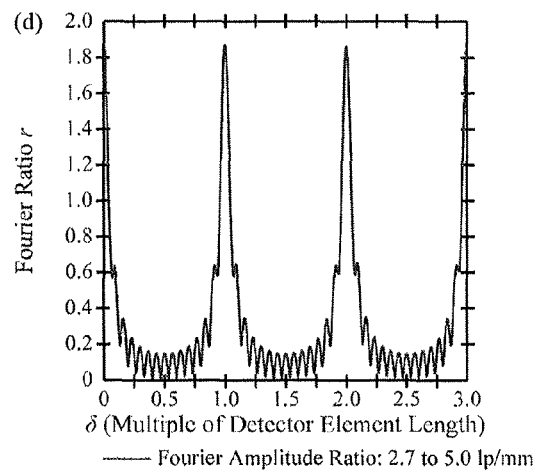

Using the Fourier transforms shown in FIGS. 8B and 8C, a metric is introduced for assessing the quality of super-resolution. This metric is the ratio (r) of the amplitude of the Fourier peaks at 2.7 to 5.0 mm$^{-1}$. Super-resolution is present if r<1 and is absent if r≥1. In FIG. 8D, the dependency of r on the increment (δ) of detector translation is analyzed. The symbol δ is a parameter that expresses the detector translation between projections as a multiple of detector element (del) length. Super-resolution may not be feasible (r>1) if detector translation between projections occurs in integer multiples of detector element length. To maximize sub-pixel sampling gain between projections, there is a range of δ values over which r is sufficiently less than unity for high quality super-resolution. For example, if the detector translation between each projection lies between 24% and 76% of detector element length, the ratio of the amplitude of the Fourier peaks at 2.7 to 5.0 mm$^{-1}$ is less than 1:5 (i.e., 20%), ensuring super-resolution quality. Super-resolution may be maximized at a displacement of δ=0.466 times the pixel length (giving r=0.010), which in the case of a detector having pixels of size 85 μm corresponds to steps of 39.6 μm.

For source (e.g., x-ray tube) trajectory implementations, the source traces an arc in the plane of the chest wall during the scan time. The r-factor described previously can be used to determine the x-ray tube translations along the PA direction that are useful for high quality super-resolution.

Figures 9A, 9B:
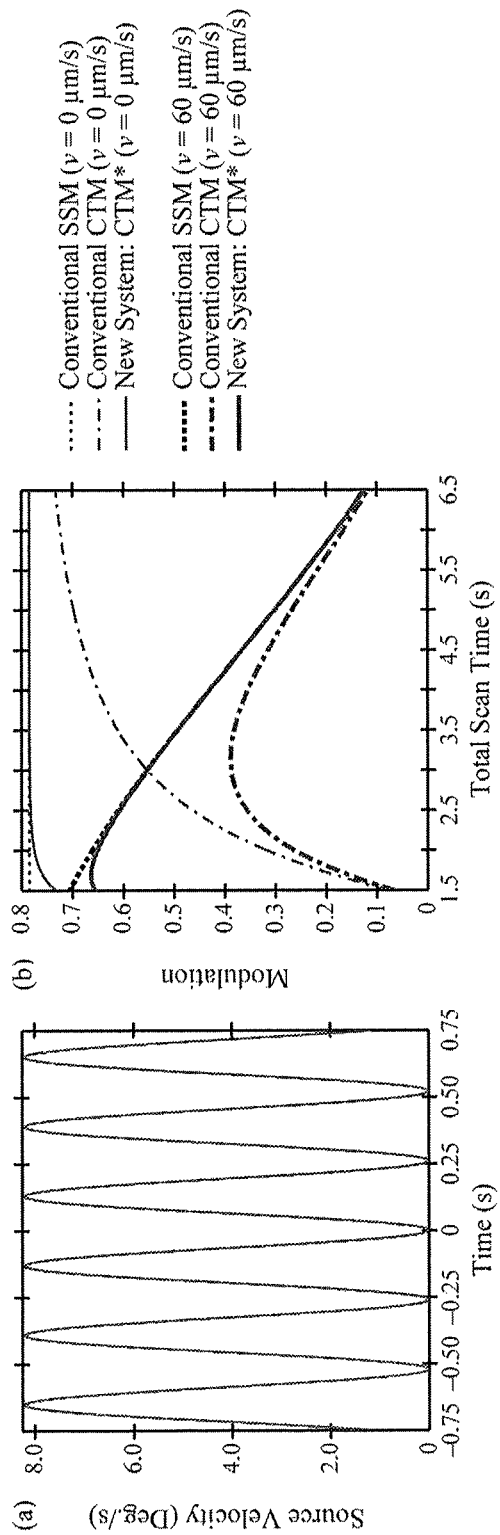
FIGS. 9A and 9B are graphs illustrating a smooth oscillatory source velocity profile that is zero during each projection to minimize blur in accordance with aspects of the invention.

In systems with continuous source motion, manufacturers typically configure the source with constant angular velocity. In an embodiment, the source 104 has an angular oscillatory velocity that varies with time (e.g., sinusoidally; see FIG. 9A). The source velocity is large between projections but approaches zero during each projection to minimize focal spot blur. In an embodiment, the velocity is the same during each acquisition of a projection on a detector. The oscillatory profile is smooth, so that there is no abrupt start-and-stop motion that would make a fast acquisition time prohibitive. This embodiment allows a system with continuous tube motion to be capable of relatively short scan times and hence less patient motion than a step-and-shoot system, but no longer have the trade-off of focal spot blurring during each projection. Although FIG. 9A illustrates that the velocity is zero during image acquisition, the velocity can be a free variable ($\omega_{min}$) that is related to the resolution desired. Analytical tools can be used to determine the optimal oscillatory profile. This data can be compared with measurements of actual oscillatory profiles of the system to ensure that the oscillatory profile is both feasible and effective.

In systems with detector motion to introduce an offset in a secondary scan direction, the detector 106 may have an oscillatory velocity similar to the velocity of the source 104. In other embodiment, given the relatively short distances used in the secondary scan direction with respect to the primary scan direction, the detector 106 may be moved at an essentially constant velocity.

To assess the improvements in image quality the modulation may be calculated at various input frequencies. For high image quality, modulation is made as large as possible. In FIG. 9B, modulation is plotted versus total scan time for a sine plate with a frequency of 2.0 mm$^{-1}$. A system with continuous source motion (e.g., continuous tube motion (CTM)) at constant angular velocity has less modulation than a comparable system with step-and-shoot motion (SSM) for any fixed scan time. This arises because SSM has no focal spot blurring. By contrast, modulation achieved with a CTM* system in accordance with embodiments of the invention is not significantly different from SSM. In fact, at scan times greater than 2.2 s, the relative difference in modulation between SSM and embodiments of the invention is less than 1.0%. A clinical DBT system with continuous tube motion and a scan time of 3.7 s is modeled as an example. In that system, the modulation is 0.63 and 0.37 for object velocities (v) of 0 and 60 μm/s, respectively. The object velocity of 60 μm/s, which models the presence of patient motion, is directed mediolaterally. In a design in accordance with embodiments of the invention, modulation for the 3.7 s scan time is 0.78 and 0.47 for the two respective object velocities, giving 24% and 27% improvements in modulation relative to existing CTM systems.

Figure 10A:
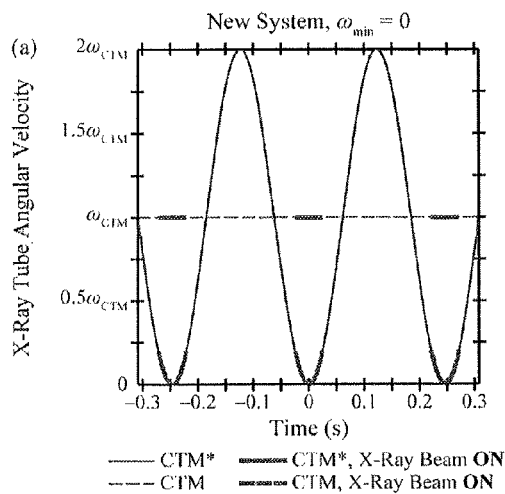
FIGS. 10A, 10B, 10C, and 10D are graphs illustrating angular source velocity and source angle with respect to time in accordance with aspects of the invention as compared to conventional systems.
Figure 10B:
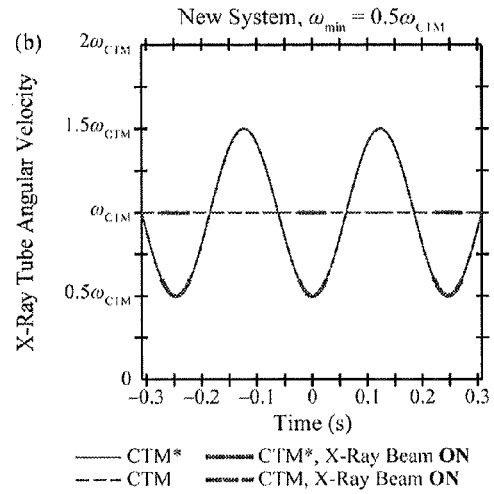

FIG. 10A depicts an embodiment in which the source velocity oscillates with time. FIGS. 10A and 10B illustrate source velocity embodiments for a tomosynthesis system with 15 projections, 1.07° spacing between projections, 50.0 ms exposure time per projection, and 3.5 s total scan time. The acquisition parameters that are modeled in FIGS. 10A and 10B are comparable to the existing Selenia Dimensions digital breast tomosynthesis system. This conventional system has continuous source motion at a constant angular velocity of 4.34°/s [this angular velocity is a horizontal line denoted $\omega_{CTM}$ in FIG. 10A]. FIGS. 10A and 10B show three of the 15 time points during which projection images are acquired, with thicker lines indicating the exposure time during each projection.

In embodiments of the invention (CTM*), the minimum value of the source velocity is a parameter ($\omega_{min}$) that controls the blurring in each projection image. In FIG. 10A, $\omega_{min}$ is set to zero, so that the motion of the source is minimal or non-existent during the exposure time of each projection image in order to minimize focal spot blurring and achieve high resolution for super-resolution tomosynthesis.

The minimum velocity of the source may be increased as illustrated in FIG. 10B, yielding greater source motion during the exposure time of the projection images. In FIG. 10B, $\omega_{min}=0.5\omega_{CTM}$. The minimum source velocity ($\omega_{min}$) can be specified based on the resolution desired. Although FIGS. 10A and 10B show only two embodiments of this design, multiple embodiments can be developed within the scope of this patent by allowing $\omega_{min}$ to attain essentially any value between zero and $\omega_{CTM}$.

Figure 10C:
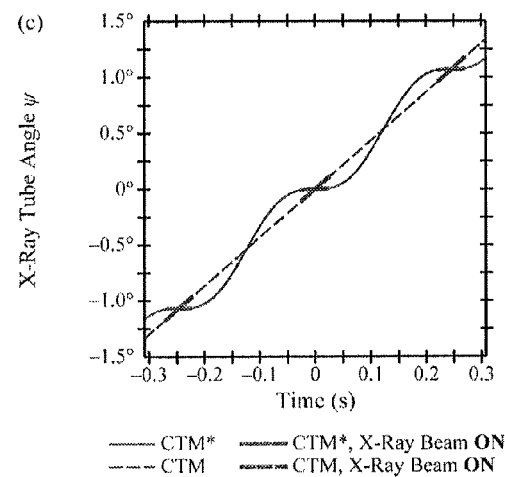

In a conventional system with continuous tube motion (CTM), the angular position of the source varies linearly with time. In embodiments of the invention with $\omega_{min}=0$, the angular position is approximately constant during the exposure time of each projection, corresponding to the plateaus shown by the thick lines in FIG. 10C. The conventional technique for generating a high-resolution image is to stop the source during the exposure time of each projection. Although the source does not stop during the exposure time in FIG. 10C, embodiments of the invention do yield minimal or non-existent source motion as shown.

Figure 10D:
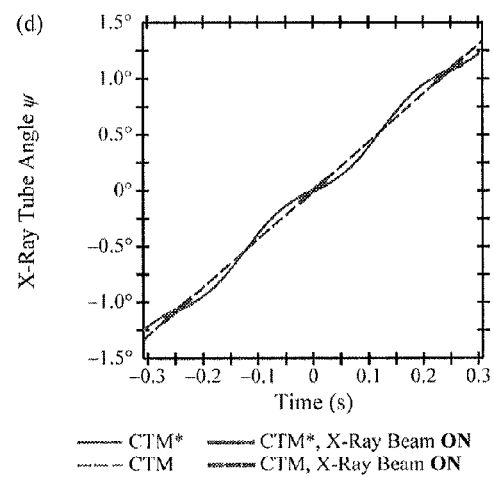

As $\omega_{min}$ increases, focal spot blurring also increases due to the non-zero velocity of the source during the exposure time. In FIG. 10D, the angular sweep of the source during the exposure time is greater than in FIG. 10C as a result of the increase in $\omega_{min}$. Thus, the choice of $\omega_{min}$ is related to the resolution desired.

Figure 11A:
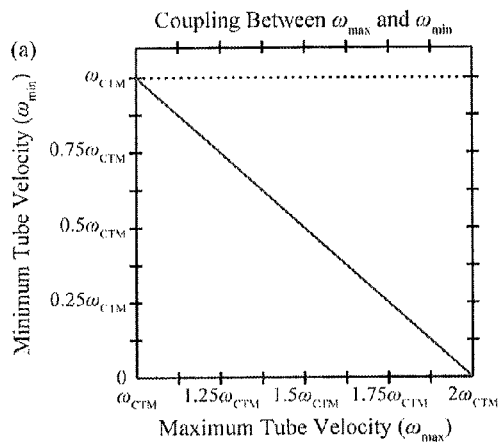
FIGS. 11A and 11B are graphs indicating the effect of source/tube velocity on blurring in accordance with aspects of the invention.

In embodiments of the invention, the minimum and maximum values of the oscillatory source velocity are coupled as depicted in FIG. 11A. In order to achieve the highest resolution ($\omega_{min}=0$), the maximum source velocity ($\omega_{max}$) is selected to be $2\omega_{CTM}$ (e.g., 8.68°/s for the acquisition geometry modeled in FIGS. 10A-10D). This maximum source velocity provides a mechanical constraint for designing a tomosynthesis system with minimal to non-existent source motion using the oscillatory source velocity. Where mechanical constraints place a limit on the maximum source velocity that is attainable, FIG. 11A illustrates that the minimum source velocity may also be constrained, thereby limiting the resolution achievable.

Figure 11B:
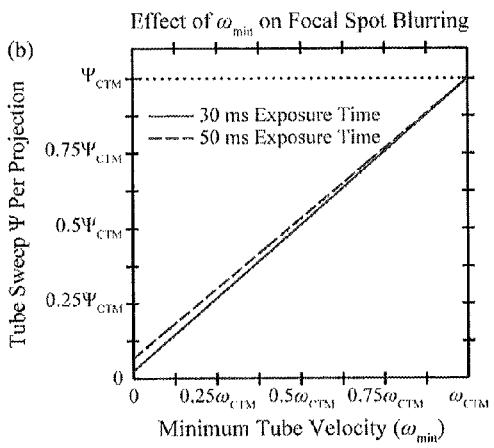

In FIG. 11B, the angular sweep of the source per projection (W) is introduced as a parameter modeling the focal spot blurring. In order to compare blurring in the CTM* system against existing systems, ψ is normalized by the corresponding value for a conventional CTM system (e.g, in the Selenia Dimensions system, ψ is 0.21°). FIG. 11B shows that the angular sweep ψ increases with increasing $\omega_{min}$, further illustrating that $\omega_{min}$ can be used to control the resolution desired for each projection image. Although an exposure time of 50.0 ms is modeled in FIGS. 10A-10D, an additional exposure time of 30.0 ms is modeled in FIG. 11B. These two exposure times are chosen since the mean and maximum exposure times for the Selenia Dimensions system are 30.0 ms and 50.0 ms, respectively. Assuming that $\omega_{min}=0$, FIG. 11B shows that the angular sweep attains 2.4% and 6.6% of the corresponding value for a conventional CTM system with constant angular source velocity (30.0 and 50.0 ms exposure times, respectively). Conversely, assuming that $\omega_{min}=0.5\omega_{CTM}$, the angular sweep LP attains 51.2% and 53.3% of the corresponding value for a conventional CTM system. Because the larger angular sweep may yield greater focal spot blurring, the resolution may depend on the choice of $\omega_{min}$. FIG. 11B illustrates that minimizing $\omega_{min}$ minimizes focal spot blurring.

Figure 11C:
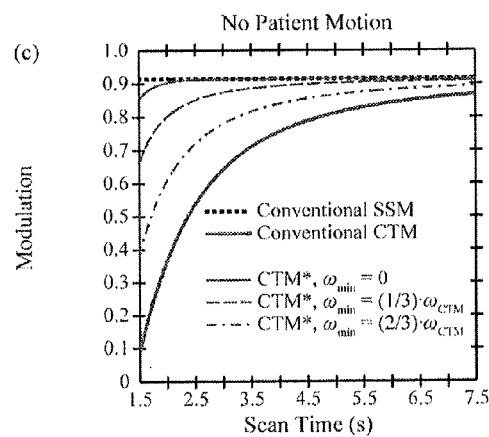
FIGS. 11C and 11D are graphs illustrating modulation versus scan time without and with patient motion for aspects of the invention compared to conventional systems.
Figure 11D:
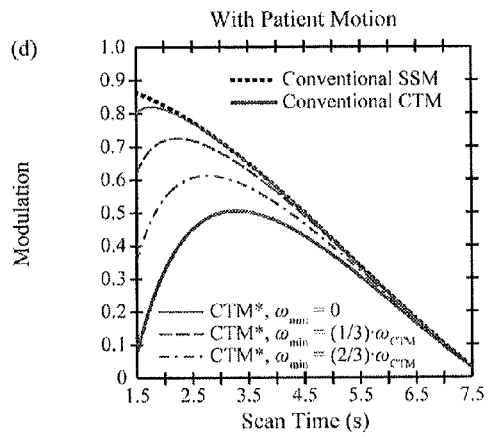

An additional metric that can be used to assess improvements in image quality in accordance with embodiments of the invention is the modulation of the reconstruction of a sine plate. Modulation may be calculated as the ratio of the amplitude of the signal in the reconstruction to the corresponding amplitude in the attenuation coefficient of the sine plate. Modulation should be preserved to demonstrate the benefits of embodiments of the invention. In FIGS. 11C and 11D, a 0.5 mm thick sine plate placed 50.0 mm above a detector is modeled assuming 100 μm detector elements, a 2.0 $mm^{-1}$ input frequency, and an object velocity v of zero (i.e., no patient motion). As expected, a conventional CTM system has less modulation than an analogous system with step-and-shoot motion (SSM) at any fixed scan time. This result is expected since SSM has no source motion during the exposure time. FIG. 11C calculates the improvement in modulation in accordance with inventive embodiments (CTM*) relative to conventional CTM. FIG. 11C demonstrates that at scan times exceeding 2.1 s, the relative difference in modulation between the CTM* system and an analogous SSM system is less than 1.0% assuming that $\omega_{min}=0$.

FIG. 11C shows that the oscillatory source velocity can be used as a tool to achieve image quality comparable to SSM. Embodiments of the invention have numerous advantages over a SSM system. First, the oscillatory source velocity does not require abrupt start-and-stop motion that gives rise to a long scan time in a SSM system. A long scan time generates greater blurring due to increased patient motion. A short scan time will also reduce patient discomfort. A SSM system is also characterized by microphonic vibrations of the source during the exposure time; these vibrations degrade image quality and are not modeled for the purpose of FIG. 11A-11D. Embodiments of the invention have an advantage over SSM by not exhibiting the microphonic vibrations due to the abrupt start and stop motion of the source.

FIG. 11C shows that the increase in modulation of CTM* relative to conventional CTM is most pronounced at values of $\omega_{min}$ approaching zero. The improvement in modulation relative to conventional CTM can thus be determined by the choice of $\omega_{min}$.

FIG. 11D generalizes the results presented in FIG. 11C to a system with patient motion assuming an object velocity v of 60 μm/s oriented along the direction of primary source motion. FIG. 11D shows that the benefits of the CTM* design relative to conventional CTM are preserved in a system with patient motion.

Figure 11E:
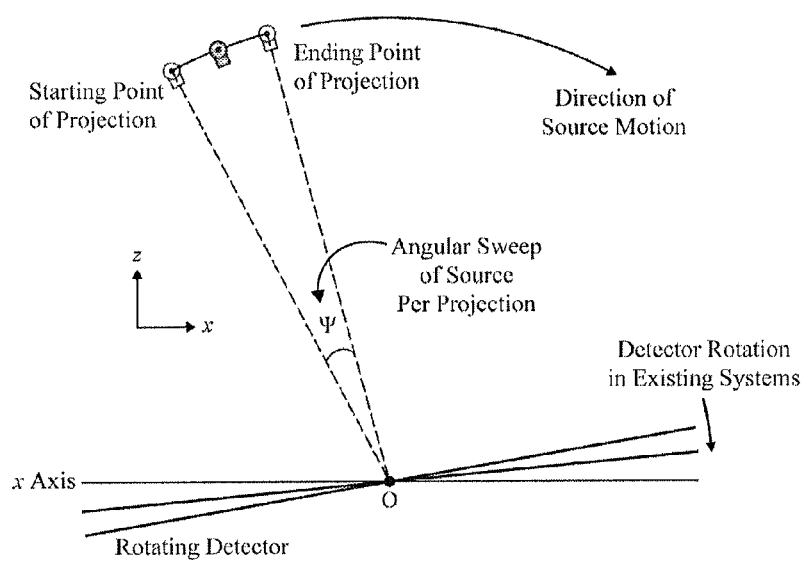
FIG. 11E is an illustration of angular sweep of the source (I)) during the exposure time of each projection in accordance with aspects of the present invention.

FIG. 11E illustrates the angular sweep of the source (ψ) during the exposure time of each projection. The angular sweep provides a measure of focal spot blurring that may be used to evaluate the benefits of embodiments of the invention against conventional systems (see FIG. 11B and related description).

Figure 12A:
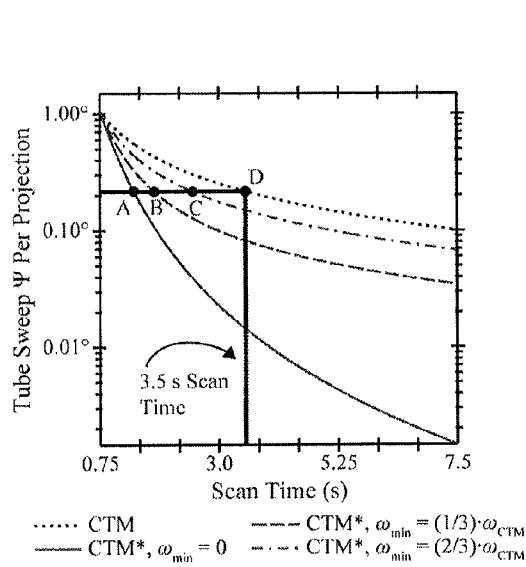
FIGS. 12A and 12B are graphs illustrating shortened scan times achievable in accordance with aspects of the invention as compared to conventional systems.

In addition to minimizing focal spot blurring, the oscillatory source velocity can be used as a tool to shorten scan time. A short scan time is important in order to minimize patient motion artifacts in tomosynthesis imaging. This property is illustrated in FIG. 12A showing the angular sweep of the source (ψ) per projection as a function of total scan time. For the purpose of this figure, it is assumed that the focal spot blurring in a conventional CTM system such as Selenia Dimensions yields acceptable image quality. The source sweep is 0.21° per projection in this conventional system with a 3.5 s scan time (Point D in FIG. 12A). A CTM* system can be operated at a much shorter scan time with the same source sweep per projection, indicating that scan time can be shortened with no change in image quality relative to existing systems. Assuming that $\omega_{min}=0$, the oscillatory source velocity can be used to shorten scan time from 3.5 s to 1.4 s (more than two-fold reduction in scan time, corresponding to Point A in FIG. 12A).

Figure 12B:
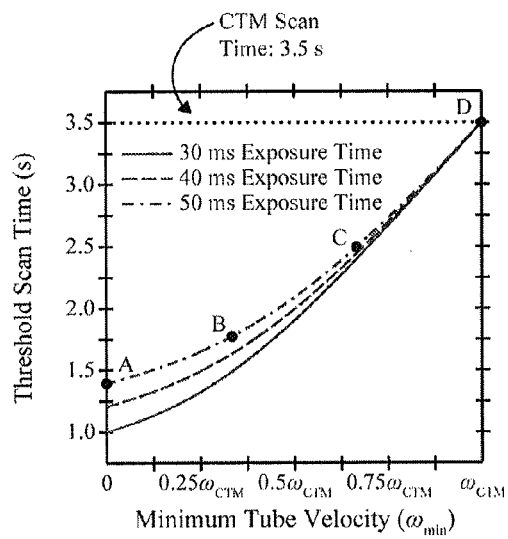

For all values of $\omega_{min}$, FIG. 12B depicts the scan time in the CTM* design that gives rise to equivalent image quality as an existing CTM system. FIG. 12B indicates that embodiments of the invention can be operated with shorter scan time than an existing CTM system for any embodiment of the oscillatory velocity profile, corresponding to all possible values of $\omega_{min}$. As shown in FIG. 12B, this result can be generalized to multiple exposure times per projection, which are shown for illustration as 30-50 ms but not necessarily limited to these exposure times in all embodiments.

Figure 13:
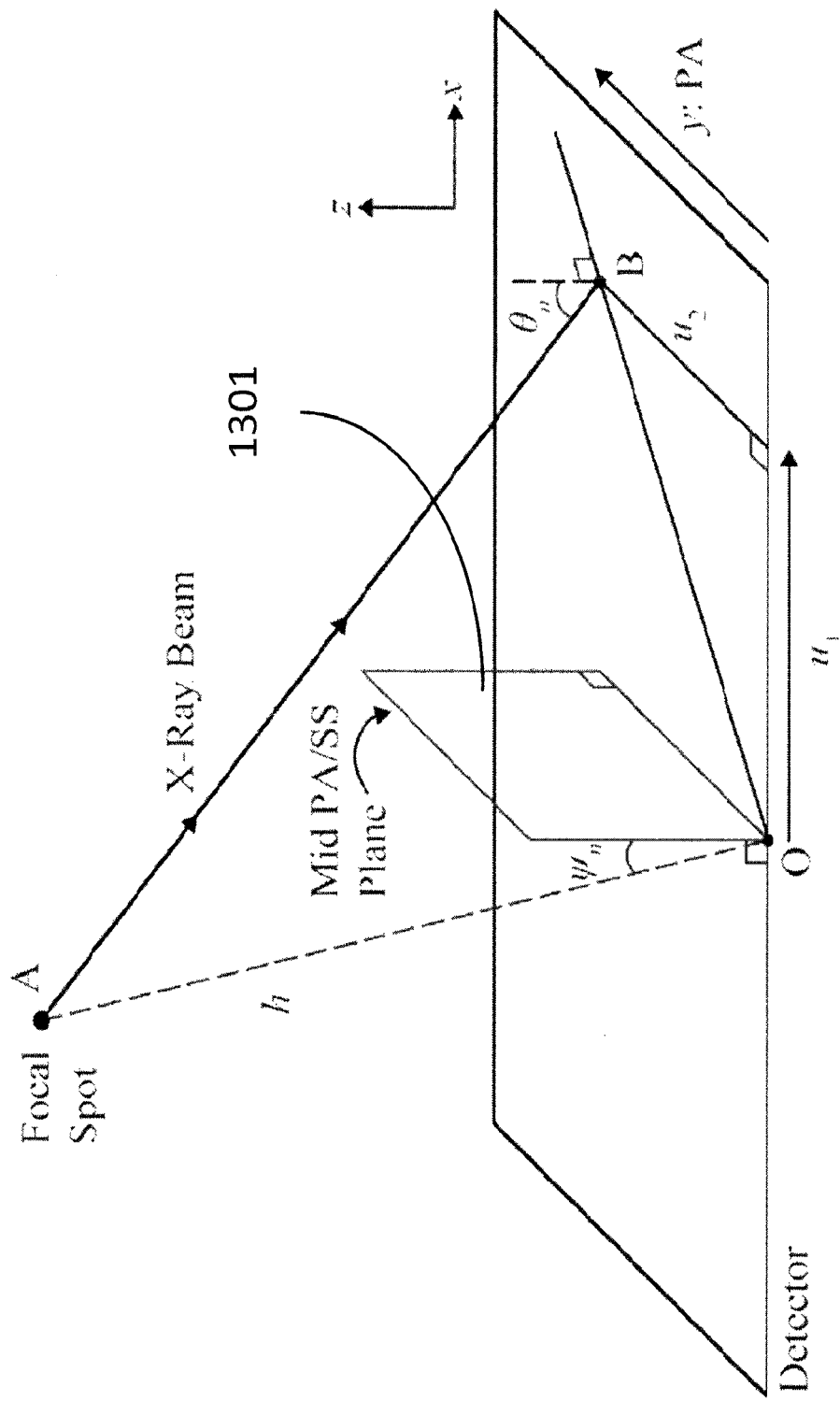
FIG. 13 is an illustration depicting the source within the plane of a chest wall in accordance with aspects of the invention.

Additional details regarding tomosynthesis for use in breast imaging are now provided. Suitable modifications for use in imaging other objects will be understood from the description herein. Achieving super-resolution depends on the directionality of the input beams and on position in the reconstruction. FIG. 13 illustrates the geometrical parameters for acquisition of x-ray projection n within the plane of the chest wall (the xz plane) at an angle $\psi_n$ relative to the z axis. With the chest wall plane as xz, the PA direction is y.

In conventional DBT implementations, super-resolution is feasible over a broad range of positions for frequencies parallel to the chest wall side of the breast support, but it is achievable at fewer positions in the PA direction. For example, super-resolution along the PA direction is not possible conventionally for input objects within a yz midplane 1301 perpendicular to the chest wall and to the breast support (FIG. 13). Since mid-plane 1301 has extent in both the PA and source-to-support (SS) direction, in embodiments of the invention mid-plane 1301 is termed the "mid PA/SS plane".

In conventional DBT implementations, super-resolution along the PA direction is not feasible in mid PA/SS plane 1301 because translational shifts in the image between projections are minimal. According to an embodiment of the invention, super-resolution is optimized via an acquisition geometry in which the detector is precisely translated in the PA direction between projections.

According to various embodiments of the invention, an analytical model of super-resolution is now developed by calculating the reconstruction of a sine input whose frequency is greater than the alias frequency of the detector.

Figure 14:
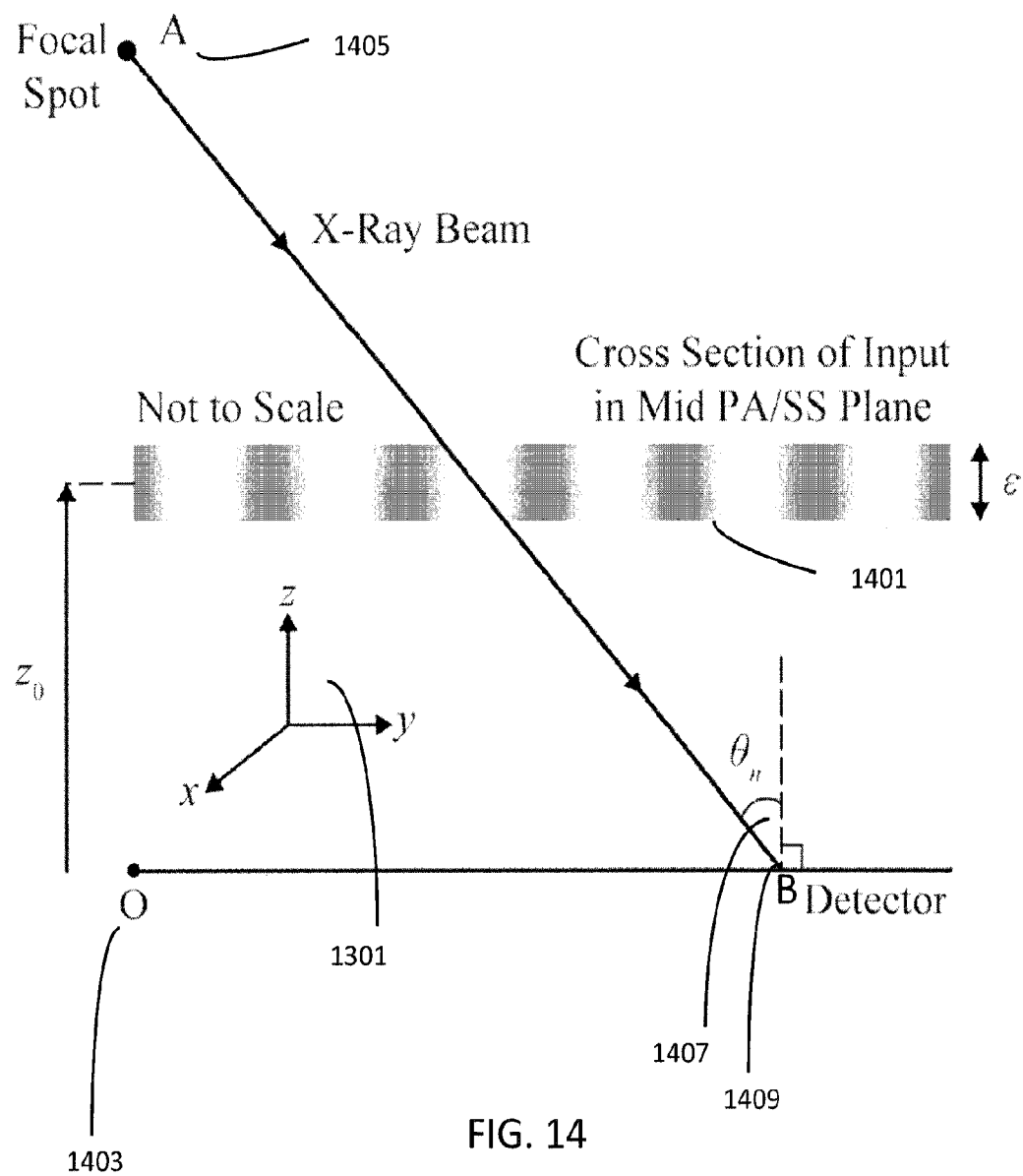
FIG. 14 is an illustration of a cross-section of a sinusoidal input object in the PA/SS plane acquisition in the central projection in accordance with aspects of the invention.

FIG. 14 illustrates a cross-section 1401 of the input in yz mid PA/SS plane 1301 acquisition in the central projection. With the xz plane as the chest wall, the input is taken to be a rectangular prism whose attenuation coefficient varies sinusoidally along the y (PA) direction. The input is positioned between the heights $Z=z_0\pm\epsilon/2$ above the detector, where $z_0$ is the central height of the input and c is its thickness (FIG. 14). Denoting C as the amplitude of the waveform and $f_0$ as its frequency, the attenuation coefficient $\mu(x,y,z)$ can be written as $C\cdot\cos(2\pi f_0 y)\cdot\text{rect}[(z-z_0)/\epsilon]$. The one-dimensional Fourier transform of the input along the y direction is a sum of delta functions peaking at the frequencies $f_y=\pm f_0$. Since only the positive frequency is of interest in a physical measurement, this input is useful for modeling the reconstruction of a single input frequency.

In DBT, x-ray projections are acquired as the x-ray source rotates in a circular arc within the plane of the chest wall. Typically, the midpoint of the chest wall side of the detector serves as the center-of-rotation (COR) of the x-ray source. Defining an origin O 1403 as the COR, the vector from O 1403 to a point A 1405 in the arc of the source is thus $\overrightarrow{OA}=(-h\sin\psi_n)i+(h\cos\psi_n)k$, where $\psi_n=n\cdot\Delta\psi$, where h denotes the source-to-origin distance, $\psi_n$ is the projection angle, n is the projection number, and $\Delta\psi$ is the angular spacing between projections. In a system with N total projections, the index n varies from $+(N-1)/2$ to $-(N-1)/2$ during the scan.

According to various embodiments of the invention, n incident angle $\theta_n$ 1407 can now be calculated at a point B 1409 on the detector. Since $\overrightarrow{OB}=u_1 i+u_2 j$, it follows that $\overrightarrow{BA}=-\overrightarrow{OB}+\overrightarrow{OA}=-(u_1+h\sin\psi_n)i-u_2 j+(h\cos\psi_n)k$, and hence incident angle $\theta_n$ 1407 can be evaluated from the dot product $$\cos\theta_n = \frac{\overrightarrow{BA}\cdot k}{|\overrightarrow{BA}||k|}, \qquad (1)$$

$$\theta_n = \arccos\left[\frac{h\cos\psi_n}{\sqrt{(u_1+h\sin\psi_n)^2+u_2^2+(h\cos\psi_n)^2}}\right]$$

The detector signal for each projection can now be determined by tracing the ray between point A 1405 and point B 1409. Defining w to be a free parameter, the equation of the ray can be written in terms of three parametric equations:

$x=w(u_1+h\sin\psi_n)-h\sin\psi_n;$ $y=wu_2;$ and $z=(1-w)h\cos\psi_n.$

The focal spot at point A 1405 is defined to correspond to w=0, and the incident point B 1409 is defined to correspond to w=1. The x-ray path length $\Lambda_n$ through the input for the $n^{th}$ projection is determined from the intersection of the incident ray with the planes $z=z_0\pm\epsilon/2$. The values of w for these two points are $w_n^\pm=1-(z_0\pm\epsilon/2)h^{-1}\sec\psi_n$.

For projection n, the total attenuation $A\mu(n)$ is given by the integral $\int\mu ds$, where ds is the differential arc length along $\Lambda_n$.

$$ds = \sqrt{\left(\frac{dx}{dw}\right)^2+\left(\frac{dy}{dw}\right)^2+\left(\frac{dz}{dw}\right)^2} \qquad (2)$$

$$dw = \sqrt{(u_1+h\sin\psi_n)^2+u_2^2+(h\cos\psi_n)^2}\,dw$$

Combining Equations (1) and (2) yields $ds=h\cos(\psi_n)\sec(\theta_n)dw$. The total x-ray attenuation at the detector position $(u_1,u_2)$ is thus $$\mathcal{A}\mu(n) = \kappa_n \int_{w_n^+}^{w_n^-}\cos(2\pi f_0 u_2 w)dw \qquad (3)$$

$$= \frac{\kappa_n[\sin(2\pi f_0 u_2 w_n^-)-\sin(2\pi f_0 u_2 w_n^+)]}{2\pi f_0 u_2},$$

where $\kappa_n=C\cdot h\cos(\psi_n)\sec(\theta_n)$. To simplify Equation (3), use the sum-to-product trigonometric identity $\sin(b_1)-\sin(b_2)=2\cos[(b_1+b_2)/2]\sin[(b_1-b_2)/2]$ for real numbers $b_1$ and $b_2$.

$$\mathcal{A}\mu(n)=\kappa_n(w_n^- - w_n^+)\cos(\pi f_0 u_2[w_n^+ + w_n^-])\text{sinc}(f_0 u_2[w_n^- - w_n^+]) \qquad (4)$$

$$= \frac{\epsilon\kappa_n\sec\psi_n}{h}\cos\left(2\pi f_0 u_2\left[1-\frac{z_0\sec\psi_n}{h}\right]\right)\text{sinc}\left(\frac{\epsilon f_0 u_2\sec\psi_n}{h}\right) \qquad (5)$$

In Equation (5), it is taken that $\sin c(u)\equiv\sin(\pi u)/(\pi m)$. This expression for total attenuation implicitly assumes that the detector possesses an x-ray converter with a modulation transfer function (MTF) of unity at all frequencies. An amorphous selenium (a-Se) photoconductor operated in drift mode is a good approximation for an x-ray converter with this property [See Lee, D. L., Cheung, L. K., Rodricks, B., Powell, G. F.: Improved imaging performance of a 14×17-inch Direct Radiography System using Se/TFT detector. In: Dobbins III, J. T., Boone, J. M. (eds.) *Proc. of SPIE, Medical*

*Imaging 1998: Physics of Medical Imaging*, vol. 3336, pp. 14-23. SPIE, Bellingham (1998), which is incorporated herein by reference].

To calculate the digitized detector signal, take into account the presence of a thin-film transistor (TFT) array which samples the total attenuation in pixels (i.e., detector elements). The logarithmically-transformed signal for projection n is obtained by averaging the signal over detector element m.

$$\mathcal{D}\mu(m, n) = \int_{a(m_y - \delta[n-(N-1)/2])}^{a(m_y+1-\delta[n-(N-1)/2])} \int_{a(m_x-1/2)}^{a(m_x+1/2)} \frac{\mathcal{A}\mu(n)}{a^2} \cdot du_1 \, du_2 \quad (6)$$

$$m_x \in \mathbb{Z}$$

$$m_y \in \mathbb{Z}^*$$

Detector elements are taken to be square with sides of length a. During the acquisition of the first projection for which n=+(N−1)/2, detector elements are centered on the coordinates $u_1=m_x a$ and $u_2=(m_y+\frac{1}{2})a$. In each subsequent projection, detector elements are translated in the PA direction (+y) by the amount δa, where δ is a translation parameter expressing the translation between projections as a fraction of detector element length. Because $\theta_n$ should not vary considerably within each detector element, total attenuation can be approximated as $$\tilde{\mathcal{A}}\mu(n) = \mathcal{A}\mu(n) \big|_{\theta_n = \theta_{mn}} \quad (7)$$

$$\theta_{mn} \equiv \theta_n \big|_{(u_1, u_2) = (m_x a, a[m_y + \frac{1}{2} - \delta(n - \frac{N-1}{2})])}$$

where $\theta_{mn}$ is the evaluation of the incident angle at the centroid of each detector element. Hence $$\mathcal{D}\mu(m, n) \cong \int_{a(m_y - \delta[n-(N-1)/2])}^{a(m_y+1-\delta[n-(N-1)/2])} \frac{\tilde{\mathcal{A}}\mu(n)}{a} \cdot du_2 \quad (8)$$

$$= \lim_{J_y \to \infty} \frac{1}{J_y} \sum_{j_y=1}^{J_y} \tilde{\mathcal{A}}\mu(j_y, n),$$

where $$\tilde{\mathcal{A}}\mu(j_y, n) \equiv \tilde{\mathcal{A}}\mu(n) \big|_{u_2 = a\left(\frac{j_y - 1/2}{J_y} + m_y - \delta[n - \frac{N-1}{2}]\right)} \quad (9)$$

In Equation (8), the midpoint formula has been used to evaluate the integral. For projection n, the signal $S\mu(u_1, u_2)$ recorded by the detector can now be written as $$S\mu(u_1, u_2) = \quad (10)$$

$$\sum_m \mathcal{D}\mu(m, n) \text{rect}\left(\frac{u_1 - m_x a}{a}\right) \text{rect}\left(\frac{u_2 - a\left(m_y + \frac{1}{2} - \delta\left[n - \frac{N-1}{2}\right]\right)}{a}\right)$$

According to various embodiments, reconstruction may be performed using this expression.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A super-resolution digital tomosynthesis system for imaging an object, the super-resolution digital tomosynthesis system comprising:
    at least one source configured to emit penetrating particles toward an object;
    at least one detector comprising an array of pixels in a detector plane configured to acquire a series of projection images of the object in response to the penetrating particles from the at least one source, pixels within the array of pixels having a fixed pixel dimension;
    a positioning apparatus configured to position the at least one source with respect to the at least one detector; and
    an imaging system coupled to the at least one source, the at least one detector, and the positioning apparatus, the imaging system configured to:
        control the positioning apparatus to position the at least one source with respect to the at least one detector to introduce a primary scan motion of the imaging system with respect to the object, wherein the primary scan motion of the source forms a primary plane, and to introduce at least one offset of the detector along a secondary direction with respect to the object, the secondary direction being in the detector plane perpendicular to the primary plane, and the at least one offset being a non-integer multiple of the pixel dimension;
        control the at least one source and the at least one detector to acquire the series of projection images with the primary scan motion and the introduced at least one offset in the secondary direction; and
        construct a tomographic volume capable of exhibiting super-resolution from data representing the acquired series of projection images taking the primary scan motion and the at least one offset into consideration.

2. The super-resolution digital tomosynthesis system of claim 1, wherein the positioning apparatus is coupled to the at least one source and the at least one detector and wherein the positioning apparatus is configured to move the at least one source in the primary scan motion and to move the at least one detector in the secondary direction.

3. The super-resolution digital tomosynthesis system of claim 2, wherein the positioning apparatus comprises:
    a first electromechanical drive coupled to the at least one source to move the at least one source along the primary scan motion;
    a second electromechanical drive coupled to the at least one detector to move the at least one detector along the secondary direction.

4. The super-resolution digital tomosynthesis system of claim 1, wherein the positioning apparatus is coupled to the at least one source and wherein the positioning apparatus is configured to move the at least one source with respect to the at least one detector, by moving the at least one source along the primary scan motion and in the secondary direction.

5. The super-resolution digital tomosynthesis system of claim 1, wherein the positioning apparatus is coupled to the at least one detector and wherein the positioning apparatus is configured to move the at least one detector with respect to the at least one source, by moving the at least one detector along the primary scan motion and in the secondary direction.

6. The super-resolution digital tomosynthesis system of claim 1, wherein the positioning apparatus comprises:

a conveyer belt configured to receive the object and to move the object in the primary scan motion past the at least one source and the at least one detector.

7. A super-resolution digital tomosynthesis method for imaging an object, the method comprising:
positioning at least one source of penetrating particles and at least one detector with respect to the object with a primary scan motion, wherein the primary scan motion of the at least one source forms a primary plane, the at least one detector comprising an array of pixels in a detector plane, pixels within the array of pixels having a fixed pixel dimension;
introducing at least one offset of the detector in a secondary direction with respect to the at least one source of penetrating particles, the secondary direction being in the detector plane perpendicular to the primary plane, and the at least one offset being a non-integer multiple of the pixel dimension;
acquiring a series of images with the primary scan motion and the introduced at least one offset; and
constructing a tomographic volume capable of exhibiting super-resolution from data representing the acquired series of projection images taking the primary scan motion and the at least one offset into consideration.

8. The super-resolution digital tomosynthesis method of claim 7, further comprising:
displaying super-resolution images from the tomographic volume.

9. The super-resolution digital tomosynthesis method of claim 7, wherein the at least one offset is introduced as the at least one source of penetrating particles is positioned with respect to at least one detector and the object with the primary scan motion.

10. The super-resolution digital tomosynthesis method of claim 7, wherein the positioning step comprises a smooth oscillatory velocity that is reduced during the acquiring of each image of the series of images.

11. The super-resolution digital tomosynthesis method of claim 7, wherein the positioning step comprises:
moving the at least one source of penetrating particles along the primary scan motion.

12. The super-resolution digital tomosynthesis method of claim 11, wherein the introducing step comprises:
moving the at least one detector along the secondary direction.

13. The super-resolution digital tomosynthesis method of claim 12, wherein the introducing step comprises:
moving the at least one source along the secondary direction.

14. The super-resolution digital tomosynthesis method of claim 11, wherein the positioning step comprises:
moving the object along the primary scan motion.

* * * * *

UNITED STATES PATENT AND TRADEMARK OFFICE
CERTIFICATE OF CORRECTION

PATENT NO. : 9,743,891 B2
APPLICATION NO. : 14/413279
DATED : August 29, 2017
INVENTOR(S) : Andrew D. A. Maidment et al.

Page 1 of 1

It is certified that error appears in the above-identified patent and that said Letters Patent is hereby corrected as shown below:

Column 1
Lines 19-23, delete "This invention was made in whole or in part with government support under Grant Number W81XWH-11-1-0100, through the Department of Defense Breast Cancer Research Program. The government may have rights in this invention." and insert --This invention was made with government support under Grant Numbers EB007140 and EB007140 awarded by the National Institutes of Health and Grant Number W81XWH-11-1-0100 awarded by the Army and the Medical Research and Material Command Office. The government has certain rights in the invention.--

Signed and Sealed this
Thirteenth Day of August, 2019

Andrei Iancu
*Director of the United States Patent and Trademark Office*